US010517934B2

(12) United States Patent
Labhasetwar

(10) Patent No.: US 10,517,934 B2
(45) Date of Patent: Dec. 31, 2019

(54) COMPOSITIONS AND METHODS FOR THE TREATMENT OF PHOTOAGING AND OTHER CONDITIONS

(71) Applicant: PRO TRANSIT NANOTHERAPY LLC, Omaha, NE (US)

(72) Inventor: Vinod D. Labhasetwar, Solon, OH (US)

(73) Assignee: ProTransit Nanotherapy, LLC, Omaha, NE (US)

( * ) Notice: Subject to any disclaimer, the term of this patent is extended or adjusted under 35 U.S.C. 154(b) by 97 days.

(21) Appl. No.: 15/506,821

(22) PCT Filed: Aug. 20, 2015

(86) PCT No.: PCT/US2015/046113
§ 371 (c)(1),
(2) Date: Feb. 27, 2017

(87) PCT Pub. No.: WO2016/032852
PCT Pub. Date: Mar. 3, 2016

(65) Prior Publication Data
US 2017/0281735 A1  Oct. 5, 2017

Related U.S. Application Data

(60) Provisional application No. 62/041,187, filed on Aug. 25, 2014.

(51) Int. Cl.
*A61K 38/44* (2006.01)
*A61Q 17/04* (2006.01)
(Continued)

(52) U.S. Cl.
CPC .......... *A61K 38/446* (2013.01); *A61K 8/0241* (2013.01); *A61K 8/29* (2013.01);
(Continued)

(58) Field of Classification Search
CPC .............. A61K 38/446; A61K 2300/00; A61K 9/5138; A61K 9/5153; A61K 31/07; A61K 31/355; A61K 31/375; A61K 38/44; A61K 2800/522; A61K 8/0241; A61K 8/29; A61K 8/66; A61K 9/0014; A61K 9/06; A61K 9/5123; A61K 31/05; A61K 31/122; A61K 31/4045; A61K 9/0019; A61K 47/59; A61K 47/6849; A61K 47/6921; A61K 31/132; A61K 31/195; A61K 31/225; A61K 31/32; A61K 31/325; A61K 31/4375; A61K 33/24; A61K 47/42; A61K 47/645; A61K 47/6455; A61K 47/6937; A61K 48/0008; A61K 48/0041; A61K 48/0083; A61K 9/0024; A61K 9/5094; A61K 9/5115; A61K 9/5146; A61K 9/5169; A61K 9/5192; A61K 31/496; A61K 31/5377; A61K 31/573; A61K 45/06; A61K 47/605; A61K 9/0048; A61K 9/0051; A61K 31/121; A61K 31/337; A61K 31/352; A61K 31/353; A61K 31/436; A61K 31/4468; A61K 31/7048; A61K 31/727; A61K 33/04; A61K 33/26; A61K 33/30; A61K 33/34; A61K 35/12; A61K 41/0038; A61K 41/0052; A61K 47/32; A61K 47/36; A61K 47/549; A61K 47/60; A61K 47/65; A61K 47/6923; A61K 47/6957; A61K 49/0054; A61K 51/06; A61K 51/1244; A61K 9/0009; A61K 9/107; A61K 9/1641; A61K 9/19; A61K 9/5052; C12Y 115/01001; C12Y 111/01006; Y10S 977/904; Y10S 977/905; Y10S 977/906; A61Q 17/04; A61Q 19/08; A61L 31/10; A61L 27/26; A61L 2300/416; A61L 31/16; A61L 2300/60; A61L 2300/624; A61L 29/085; A61L 29/126; A61L 31/129; A61L 2300/21; A61L 2300/41; A61L 2300/42; A61L 2300/602; A61L 2300/604; A61L 2300/608; A61L 2300/61; A61L 2400/06; A61L 27/16; A61L 27/20; A61L 27/52; A61L 27/54; A61L 29/146; A61L 29/148; A61L 31/146; A61L 31/148; A61L 33/08; C08L 67/04; C08L 29/04; C08L 39/06; C08L 5/08; C08L 5/10; C12N 15/111; C12N 15/86; C12N 2320/32; C12N 2710/10343; A61B 2034/105; A61B 5/103; A61B 5/1079; A61F 2/02; A61F 2/12;
(Continued)

(56) References Cited

U.S. PATENT DOCUMENTS 7,332,159 B2  2/2008 Labhasetwar et al.
7,727,554 B2  6/2010 Labhasetwar et al.
(Continued)

FOREIGN PATENT DOCUMENTS

WO      110302    * 8/2012
WO      124142    * 8/2014

OTHER PUBLICATIONS

Stees, M., et al., "A Method for Quantification of Penetration of Nanoparticles through Skin Layers Using Near-Infrared Optical Imaging" Cosmetics (2015) 2:225-235.
(Continued)

Primary Examiner — Deborah K Ware
(74) Attorney, Agent, or Firm — Robert C. Netter, Jr.; Dann, Dorfman, Herrell & Skillman

(57) ABSTRACT

Compositions and methods for the treatment of skin disorders or disease are provided.

26 Claims, 15 Drawing Sheets

Figure 1A:
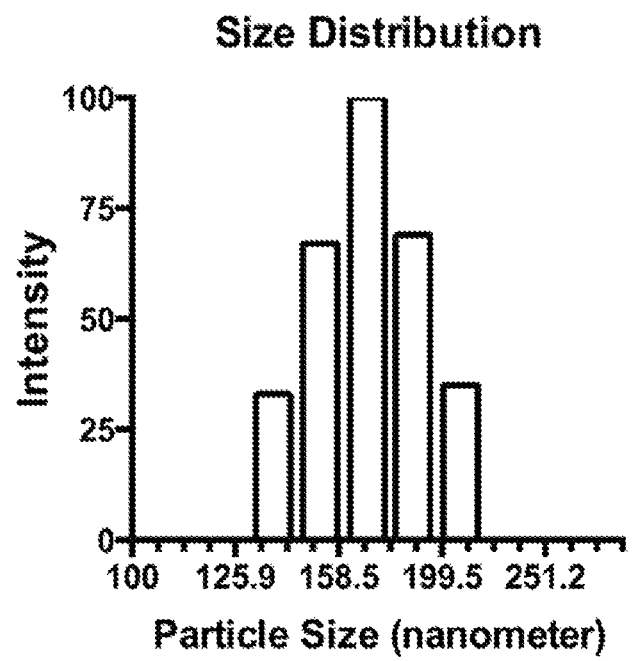

(51) Int. Cl.
*A61K 9/00* (2006.01)
*A61K 9/51* (2006.01)
*A61K 8/29* (2006.01)
*A61K 9/06* (2006.01)
*A61K 8/02* (2006.01)
*A61K 8/66* (2006.01)
*A61Q 19/08* (2006.01)

(52) U.S. Cl.
CPC .............. *A61K 8/66* (2013.01); *A61K 9/0014* (2013.01); *A61K 9/06* (2013.01); *A61K 9/5123* (2013.01); *A61K 9/5138* (2013.01); *A61K 9/5153* (2013.01); *A61K 38/44* (2013.01); *A61Q 17/04* (2013.01); *A61Q 19/08* (2013.01); *C12Y 111/01006* (2013.01); *C12Y 115/01001* (2013.01); *A61K 2800/522* (2013.01)

(58) Field of Classification Search
CPC ......... A61M 5/1723; A61M 5/20; C01G 7/00; G06F 19/00; G06F 19/30
See application file for complete search history.

(56) References Cited

U.S. PATENT DOCUMENTS

| | | | |
|---|---|---|---|
| 2006/0067925 A1 | 3/2006 | Labhasetwar et al. | |
| 2009/0136585 A1* | 5/2009 | Labhasetwar | A61K 9/5146 424/501 |
| 2009/0142408 A1* | 6/2009 | Lin | A61K 9/14 424/501 |
| 2014/0155961 A1* | 6/2014 | Morariu | A61K 8/41 607/88 |
| 2015/0139906 A1 | 5/2015 | Labhasetwar et al. | |
| 2016/0030402 A1 | 2/2016 | Labhasetwar et al. | |

OTHER PUBLICATIONS

Singhal, A., et al., "Nanoparticle-mediated catalase delivery protects human neurons from oxidative stress" Cell Death and Disease (2013) 4:e903.

Adjei, I.M., et al., "Heterogeneity in nanoparticles influences biodistribution and targeting" Nanomedicine (Lond) (2014) 9(2):267-78.

* cited by examiner

COMPOSITIONS AND METHODS FOR THE TREATMENT OF PHOTOAGING AND OTHER CONDITIONS

This application is a § 371 application of PCT/US2015/046113, filed Aug. 20, 2015, which claims priority under 35 U.S.C. § 119(e) to U.S. Provisional Patent Application No. 62/041,187, filed on Aug. 25, 2014. The foregoing applications are incorporated by reference herein.

FIELD OF THE INVENTION

The present invention relates to the treatment, inhibition, and/or prevention of skin diseases or disorders.

BACKGROUND OF THE INVENTION

Dermatological use of nanoparticles has shown promise for the delivery of drugs and other therapeutic agents for both medical and cosmetic purposes (Nohynek et al. (2008) Skin Pharmacol. Physiol., 21:136-149). There has already been successful commercialization of nanoparticle-based products in the dermatological field, including sunscreen formulations and vitamin A products (Prow et al. (2011) Adv. Drug Deliv. Rev., 63: 470-491). Various therapeutic and cosmetic applications of nanoparticles have been described as well as the need for developing a method that can determine penetration of nanoparticles through skin layers (DeLouise, L. A. (2012) J. Investig. Dermatol., 132: 964-975). Most applications of nanoparticle-based delivery systems in the dermatological field to date have been for treating skin cancer, wound healing, and delivery of antimicrobial agents (Prow et al. (2011) Adv. Drug Deliv. Rev., 63: 470-491; DeLouise, L. A. (2012) J. Investig. Dermatol., 132:964-975). In addition, nanoparticles can be applied topically for systemic delivery of drugs, such as Estrasorb®, a commercial formulation that uses topical application of an emulsion for systemic delivery of estradiol (Lee et al., Micellar nanoparticles: Applications for topical and passive transdermal drug delivery. In *Handbook of Non-Invasive Drug Delivery Systems*; Kulkarni, V. S., Ed.; Elsevier, Inc.: Amsterdam, Netherlands, 2010; pp. 37-58). Titanium dioxide and zinc oxide nanoparticles are also commonly used in sunscreen products to protect the skin from sun's ultraviolet (UV) radiation, which is considered to be the main cause of skin cancer (Smijs et al. (2011) Nanotechnol. Sci. Appl., 4:95-112).

Ultraviolet (UV) irradiation from the sun, the primary cause of most skin cancer, results in oxidative stress that can overwhelm the skin's natural antioxidant defense mechanisms, leading to significant reactive oxygen species (ROS) generation. ROS cause DNA damage that can result in gene mutations and also indirectly activate oncogenic signaling pathways. Sunscreens and skincare products commonly employed for sun protection are inadequate because they break down when exposed to UV radiation, need frequent reapplication and are particularly poor at blocking the long wavelength UVA that produces much of the ROS. In addition, topical antioxidants that are currently available commercially have poor stability after application and following UV exposure and do not penetrate the skin to reach the cells that are at risk for oncogenic transformation. The rate of cutaneous squamous cell carcinoma (SCC) has been rapidly rising due to increased exposure to ultraviolet (UV) radiation, the primary cause of skin cancer (Karia et al. (2013) J. Am. Acad. Dermatol., 68:957-966). Delivery of antioxidants in active form through skin layers and maintaining their protective effect has been challenging because of their limited stability and permeability through skin layers. Thus, there remains a strong need to develop applications designed to deliver nanoparticles and the drugs incorporated in them past the skin's outer surface into deeper tissues (DeLouise, L. A. (2012) J. Investig. Dermatol., 132:964-975; Zhang et al. (2010) Int. J. Pharm., 402:205-212) to sustain the effect of the treatment. Effective delivery of biological agents to deep layers of the skin and maintaining their activity for a sustained period that could play a protective role and facilitate skin repair/regeneration remains a challenge. Indeed, there is no such skin care product currently available in the market that contains biologically active molecules in a nanoparticle formulation (Halliday et al. (2012) J. Invest. Dermatol., 132(2):265-267; Panyam et al. (2003) Adv. Drug Deliv. Rev., 55(3):329-347).

SUMMARY OF THE INVENTION

In accordance with the instant invention, methods for delivering compounds (e.g., proteins, enzymes, protective cytokines, biological agents, etc.) to the skin, particularly beneath the stratum corneum or the epidermis, are provided. The methods may be used for treating, inhibiting, and/or preventing a skin disease or disorder or facilitating regeneration and repair of the damaged skin. In a particular embodiment, the method comprises topically administering at least one nanoparticle to the skin of the subject, wherein the nanoparticle comprises at least one biodegradable polymer and at least one antioxidant enzyme. In a particular embodiment, the nanoparticles are administered before and/or after damage to the skin (e.g., the nanoparticles can be administered as a preventive measure and/or administered to promote healing (e.g., the nanoparticles are administered to damaged skin)). The antioxidant enzyme may be catalase, glutathione peroxidase, and/or superoxide dismutase and may be sourced from natural form or expressed recombinantly from several organisms. The biodegradable polymer may be poly (lactide-co-glycolide), polylactide, or derivatives thereof. The nanoparticle may further comprise at least one plasticizer (e.g., dimethyl tartrate). The skin disease or disorder may be ultraviolet radiation induced, including, for example, photoaging, skin cancer, or sunburn or skin diseases where an important component of pathology is due to excessive free radical formation, including rosacea, psoriasis, acne, etc. The methods of the instant invention may also comprise the administration of at least one other therapeutic agent (e.g., an antioxidant, vitamin, plant derived product (e.g., phytophenols), protective cytokines (e.g., erythropoietin [EPO]), anti-inflammatory agents (e.g., steroids or non-steroidal), growth factors (e.g., VEGF, bTGF, etc.), pain medication (e.g., capsaicin, diclofenac lidocaine, etc), antibacterial agent (e.g., sulfacetamide, erythromycin, silver nanoparticles, etc.), antifungal agents (e.g., tolnaftate, benzoic acid/salicylic acid, ketoconazole, etc.), proteases or protease blend (e.g., serine proteases, cysteine proteases, aspartate proteases, threonine proteases, glutamic acid proteases, and metalloproteases, etc.), protease inhibitors (e.g. tipranavir, ritonavir, etc.), and nucleic acids (e.g. DNA, RNA, siRNA, etc.)). The methods of the instant invention may also comprise the administration of at least one metal oxide nanoparticle (e.g. titanium dioxide, zinc oxide). In a particular embodiment, the method comprises administering nanoparticles comprising at least one biodegradable polymer and catalase, and nanoparticles comprising at least one biodegradable polymer and superoxide dismutase. The nanoparticles may be administered using a suitable base for topical application (e.g., lotion, cream, ointment, adhesive bandage, etc). The base may be water-in-oil (w/o), oil-in-water (o/w), water-in-oil-in-water (w/o/w), anhydrous, or a combination of different bases. The base may be polymeric or natural hydrogel or films, which may be prepared before application or form in situ following application. The base may contain a skin permeation enhancer (e.g., surfactants (e.g., polysorbates, CTAB, DMAB), solvents (e.g., benzyl alcohol, isopropyl alcohol)), moisturizer, lubricant, color, dye, etc. In addition, ultrasound or laser exposure before, during, and/or after application can be used to facilitate the transport of nanoparticles and applied therapy.

In accordance with another aspect of the instant invention, topical compositions are provided which are well-suited for the delivery of compounds to the skin (e.g., beneath the stratum corneum and/or epidermis). In a particular embodiment, the topical composition comprises at least one carrier (e.g., a carrier acceptable for topical delivery (e.g., a pharmaceutically and/or cosmetically acceptable carrier), nanoparticles comprising at least one biodegradable polymer and catalase, and nanoparticles comprising at least one biodegradable polymer and superoxide dismutase.

BRIEF DESCRIPTIONS OF THE DRAWING

FIG. 1A provides a Gaussian distribution of nanoparticles. Nanoparticles had a mean hydrodynamic diameter of 165 nm with a polydispersity index of 0.135.

Figure 1B:
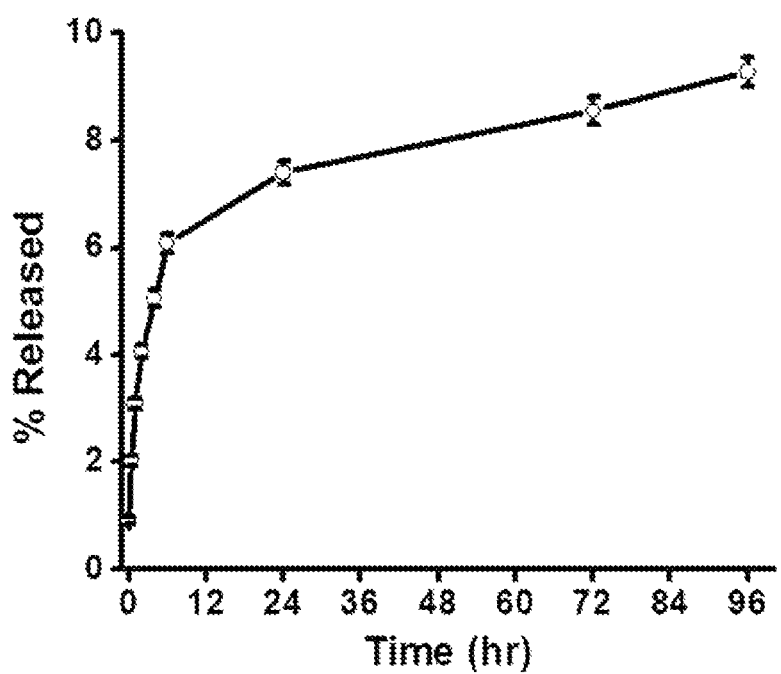

FIG. 1B shows dye release from nanoparticles in buffer under in vitro conditions. Nanoparticles in release buffer released less than 10% of their total incorporated dye in 96 hours. Data show mean±standard error, with n=3.

Figure 2A:
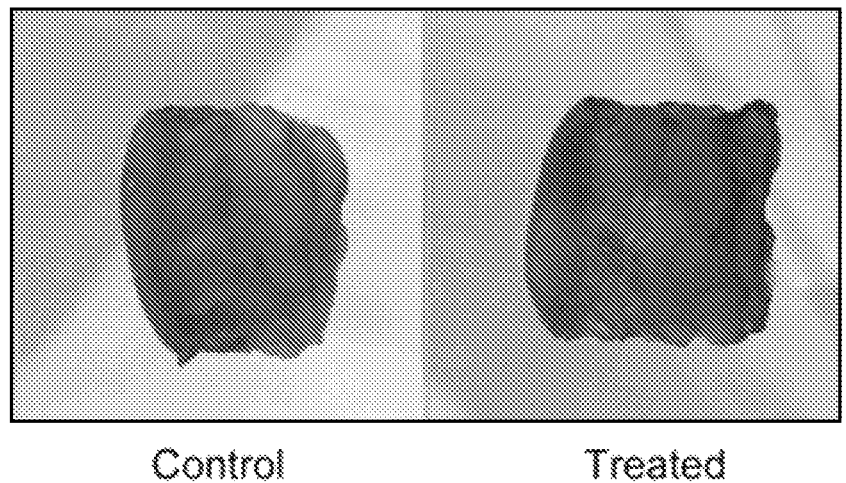
Figure 2B:
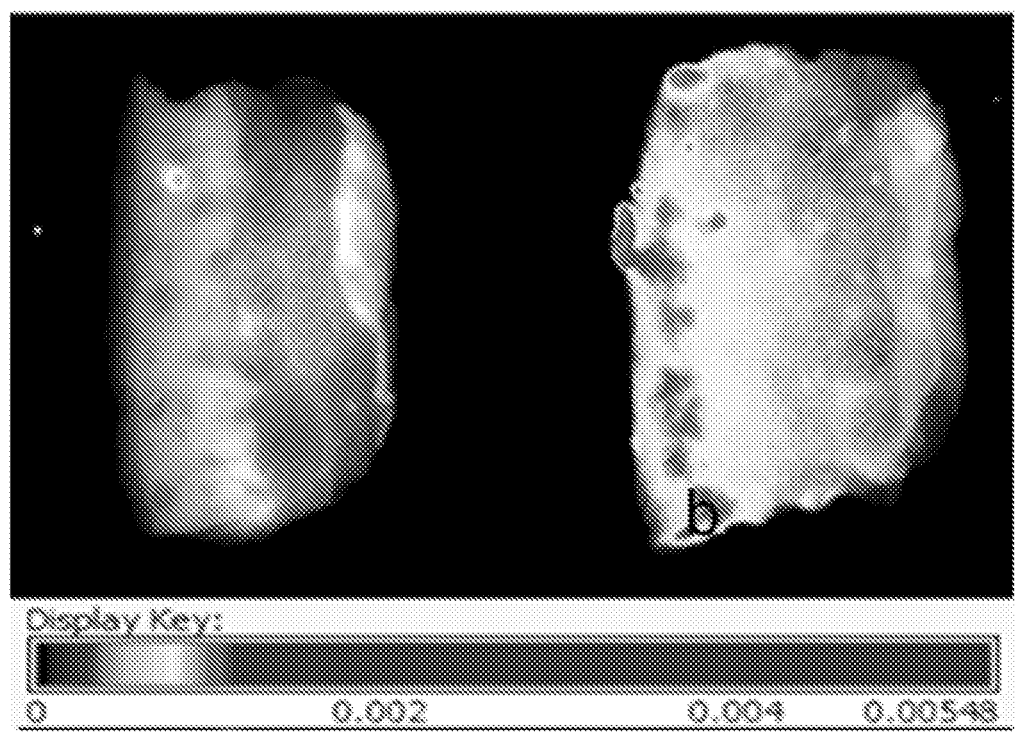
Figure 2C:
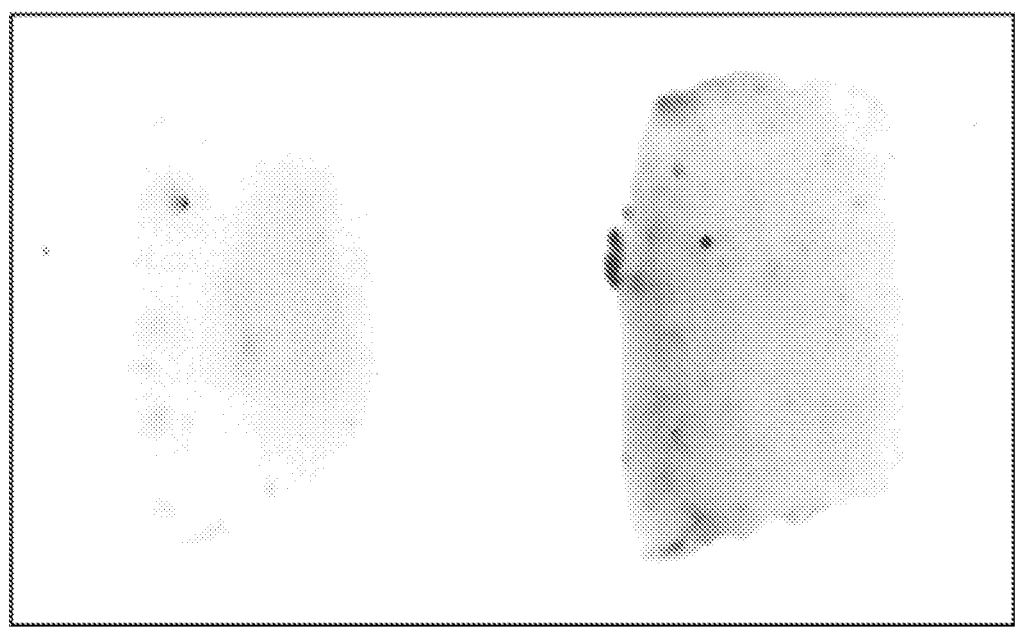

FIGS. 2A-2C provide images of skin specimens. Each pair has the control specimen on the left (treated with cream only) and the treated specimen on the right (treated by application of dye-containing nanoparticles in cream). The epidermal surface is on the left for all specimens. Notably, the specimens in FIGS. 2B and 2C are the same pair of specimens, while FIG. 2A depicts a different pair. FIG. 2A shows skin specimens mounted between glass slides for imaging. Each pair of specimens, after treatment with nanoparticles mixed into skin cream, was mounted between glass microscope slides in a package that compressed the samples uniformly and held them stably in place for imaging on both sides. FIG. 2B provides skin specimens with fluorescence signal translated to heat maps. Warm colors (high fluorescence signal) and cool colors (low fluorescence signal) demonstrate clear diffusion of near-infrared signal through the treated specimen. FIG. 2C provides skin specimens with near-infrared signal intensity shown in one color. The control specimen has very little signal while the treated specimen shows reducing intensity moving from epidermal surface to dermis.

Figure 3A:
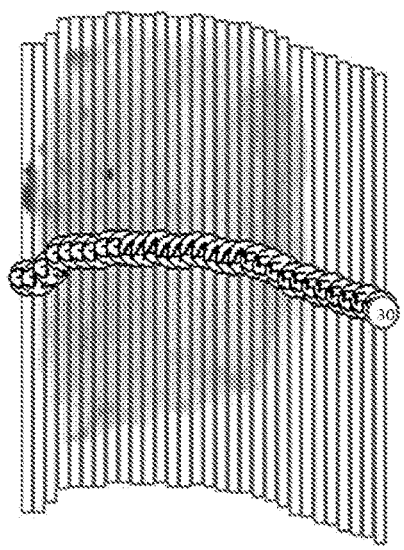
Figure 3B:
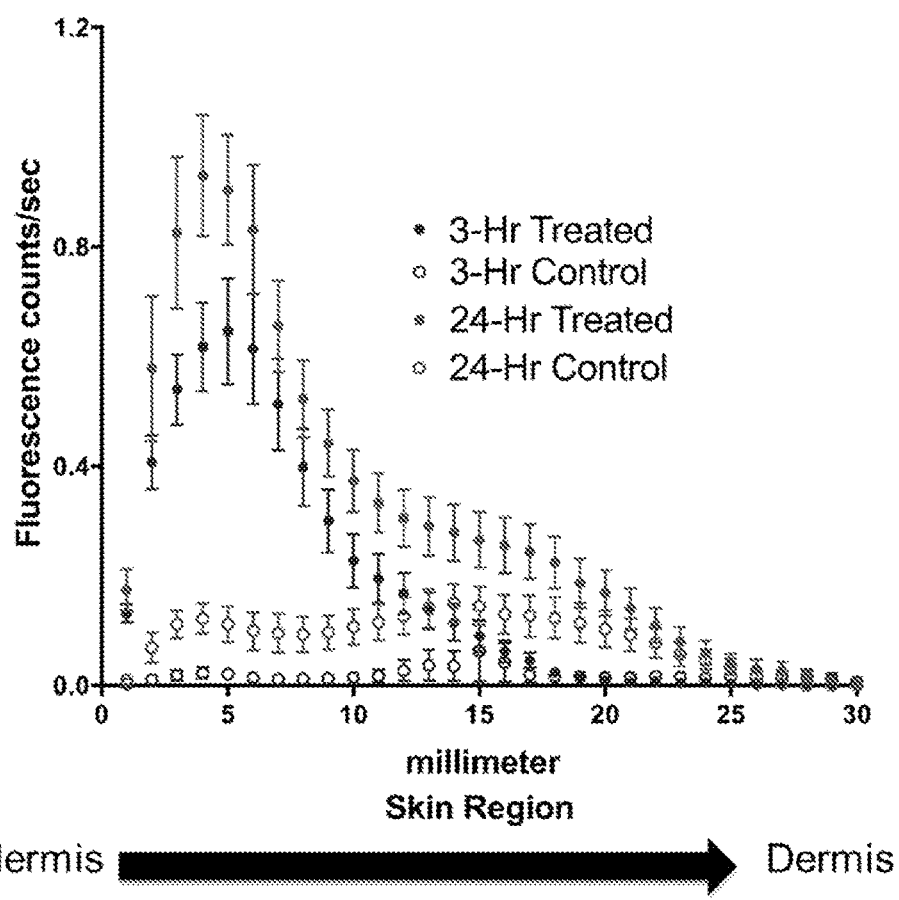

FIGS. 3A and 3B show digital sectioning and quantification of penetration of nanoparticles through skin specimens. FIG. 3A provides an illustration of digital sectioning for quantification of near-infrared signal through skin layers. The fluorescence image of each specimen was divided into a uniform set of thirty 0.5 mm-wide, vertical regions spanning the entire cross-section of the specimen, and the signal was quantified for each region. FIG. 3B shows the quantification of signal intensity through skin layers following 3-hour and 24-hour incubations. Quantified near-infrared signals for each group show progression of the signal well into the skin in a characteristic diffusion gradient pattern. The control specimens consistently displayed a lower signal than the treated specimens. Incubation with nanoparticle cream for 24 hours produced higher signal than 3-hour incubation. Data show mean±standard error, with n=12 for 3-hour incubation, n=16 for 24-hour incubation.

Figure 4A:
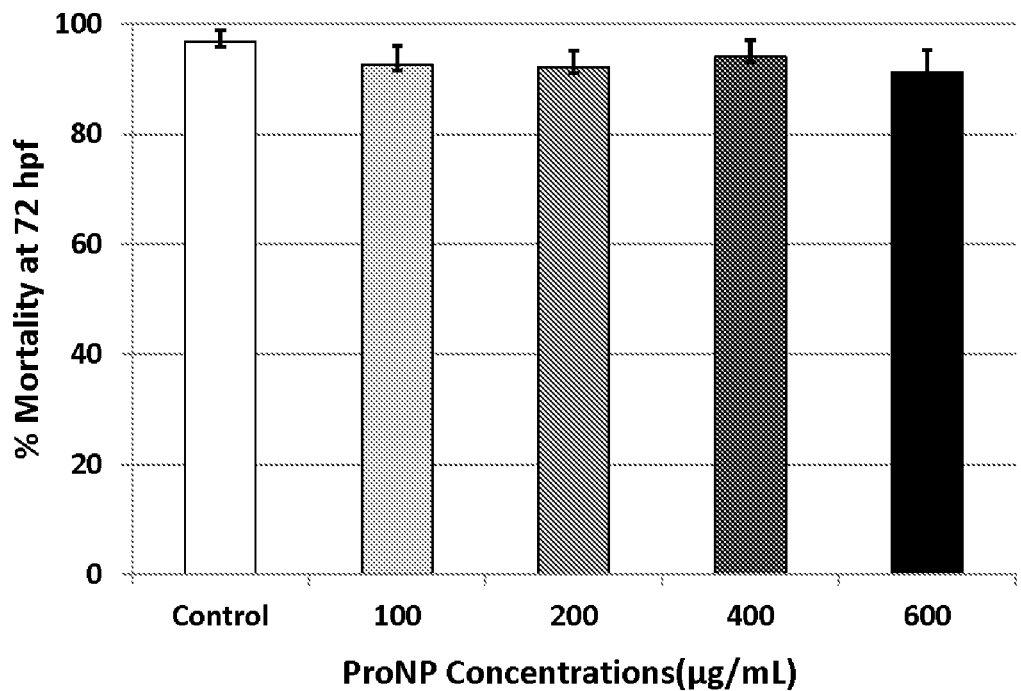
Figure 4A:
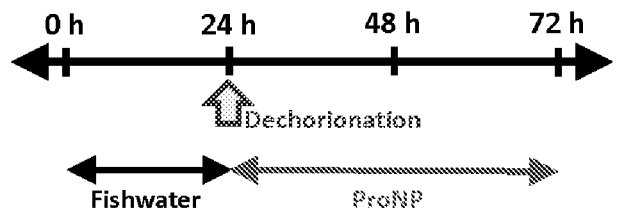
Figure 4B:
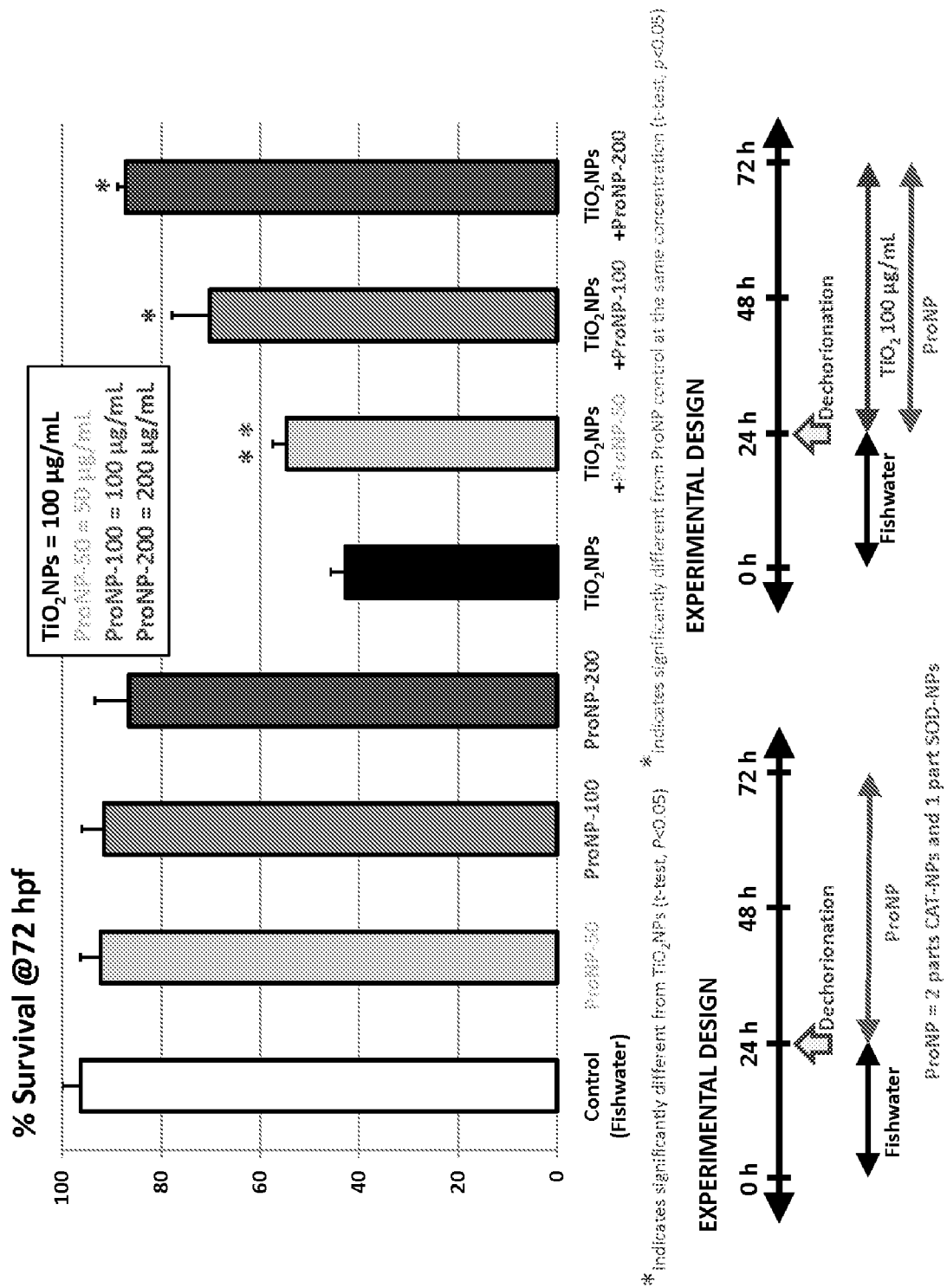
Figure 4C:
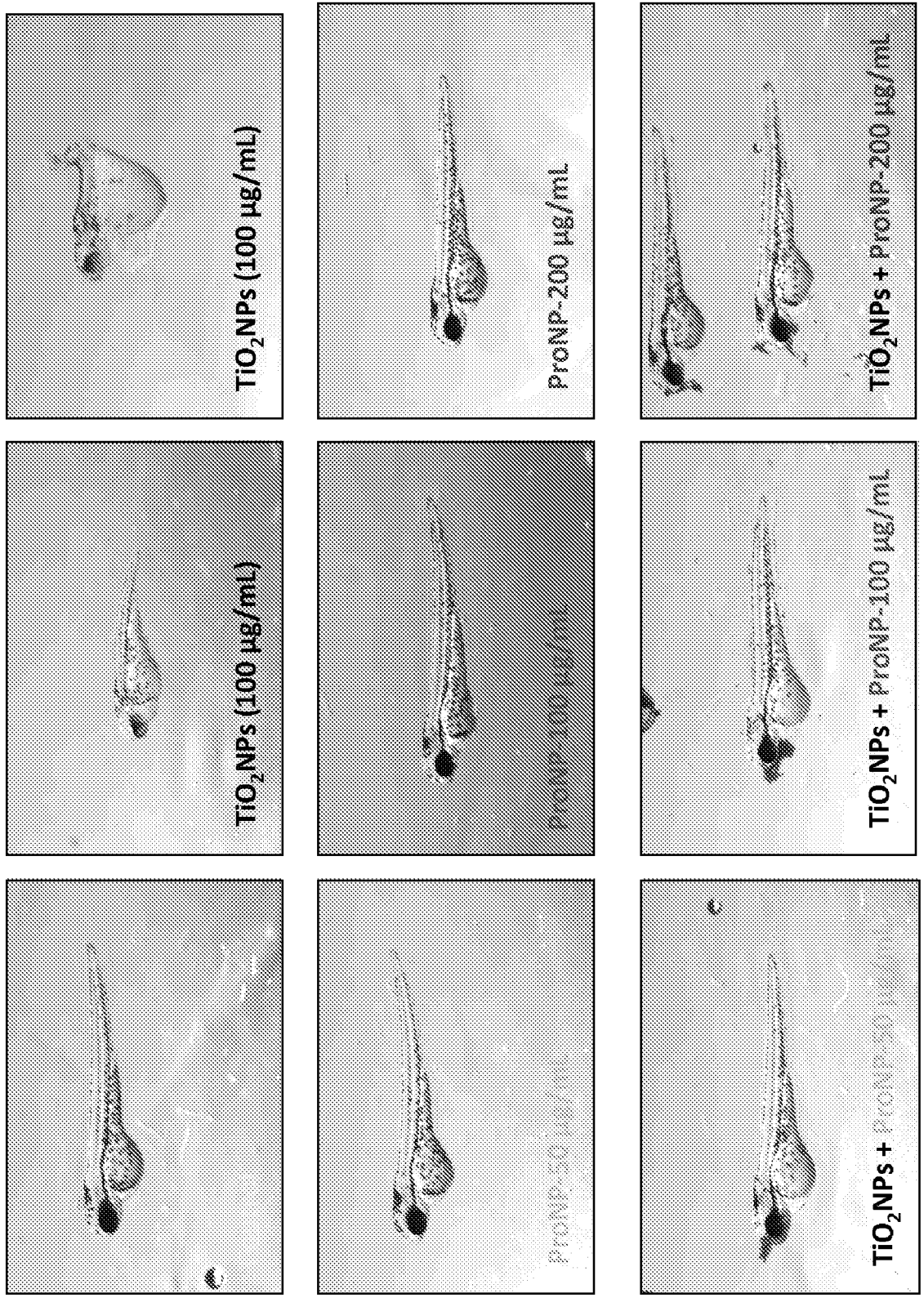

FIG. 4A provides a graph of the survival of zebrafish after exposure to Pro-NP™ at various concentrations. Here, the Pro-NP™ formulation comprises superoxide dismutase (SOD) and catalase (CAT) loaded nanoparticles which were prepared separately and mixed together (although Pro-NP™ can be prepared whereby both SOD and CAT together are encapsulated in a single nanoparticle formulation). Here, the ratio of the two formulations was 1:2 w/w. Pro-NP™ is designed to sustain the effect of antioxidant enzymes following their diffusion through skin layers. A schematic of the experimental design is also provided. FIG. 4B provides a graph of the survival of zebrafish after exposure to $TiO_2$ nanoparticles, Pro-NP™, or a combination thereof at various concentrations. A schematic of the experimental design is also provided. FIG. 4C provides images of zebrafish after exposure to $TiO_2$ nanoparticles, Pro-NP™, or a combination thereof at various concentrations.

Figure 5A:
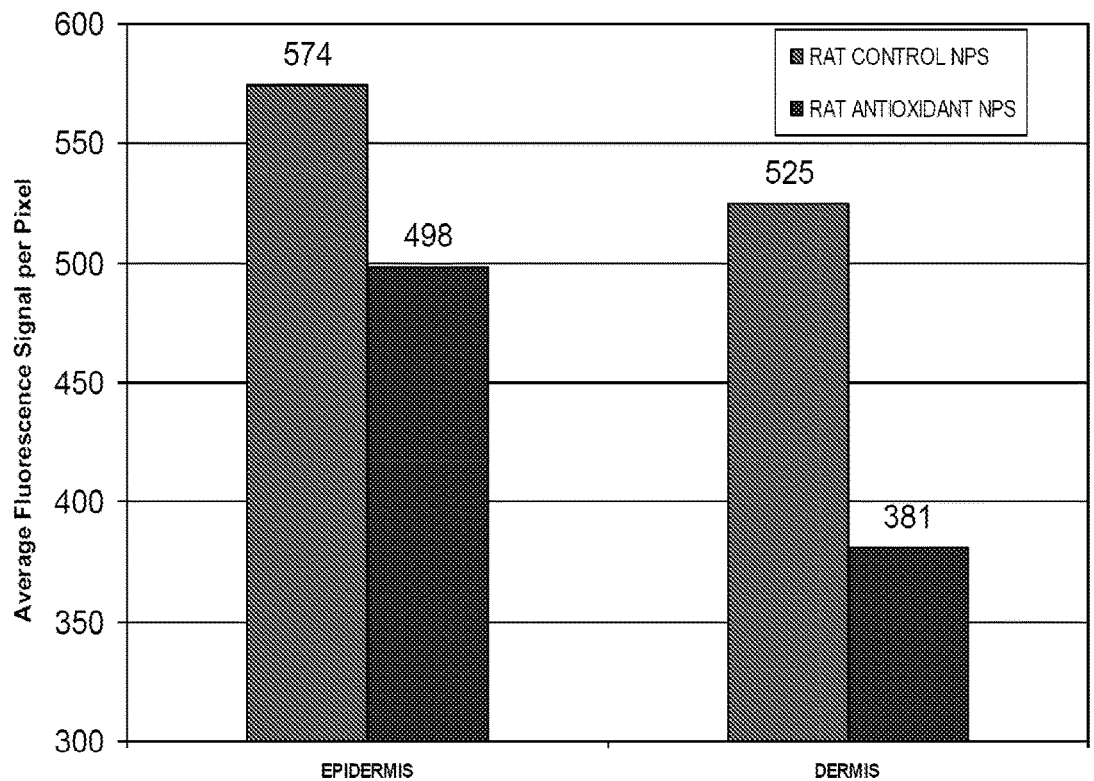
Figure 5B:
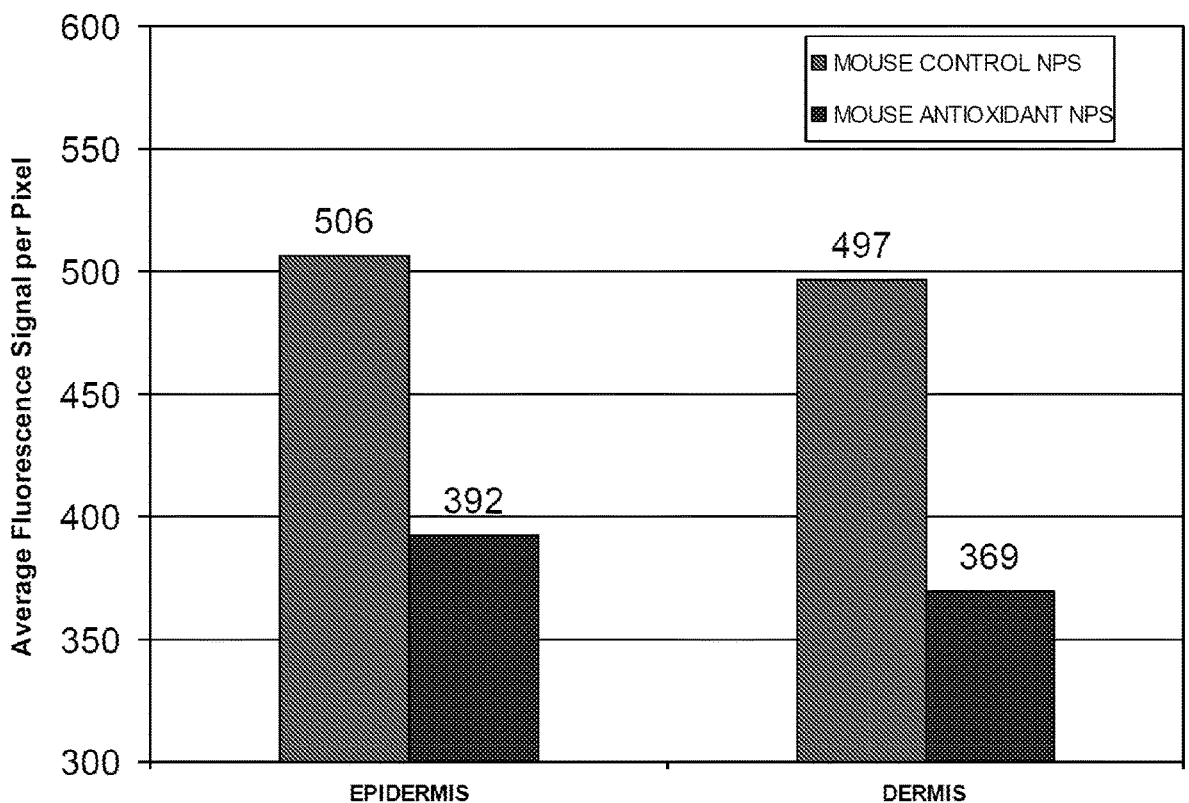
Figure 5C:
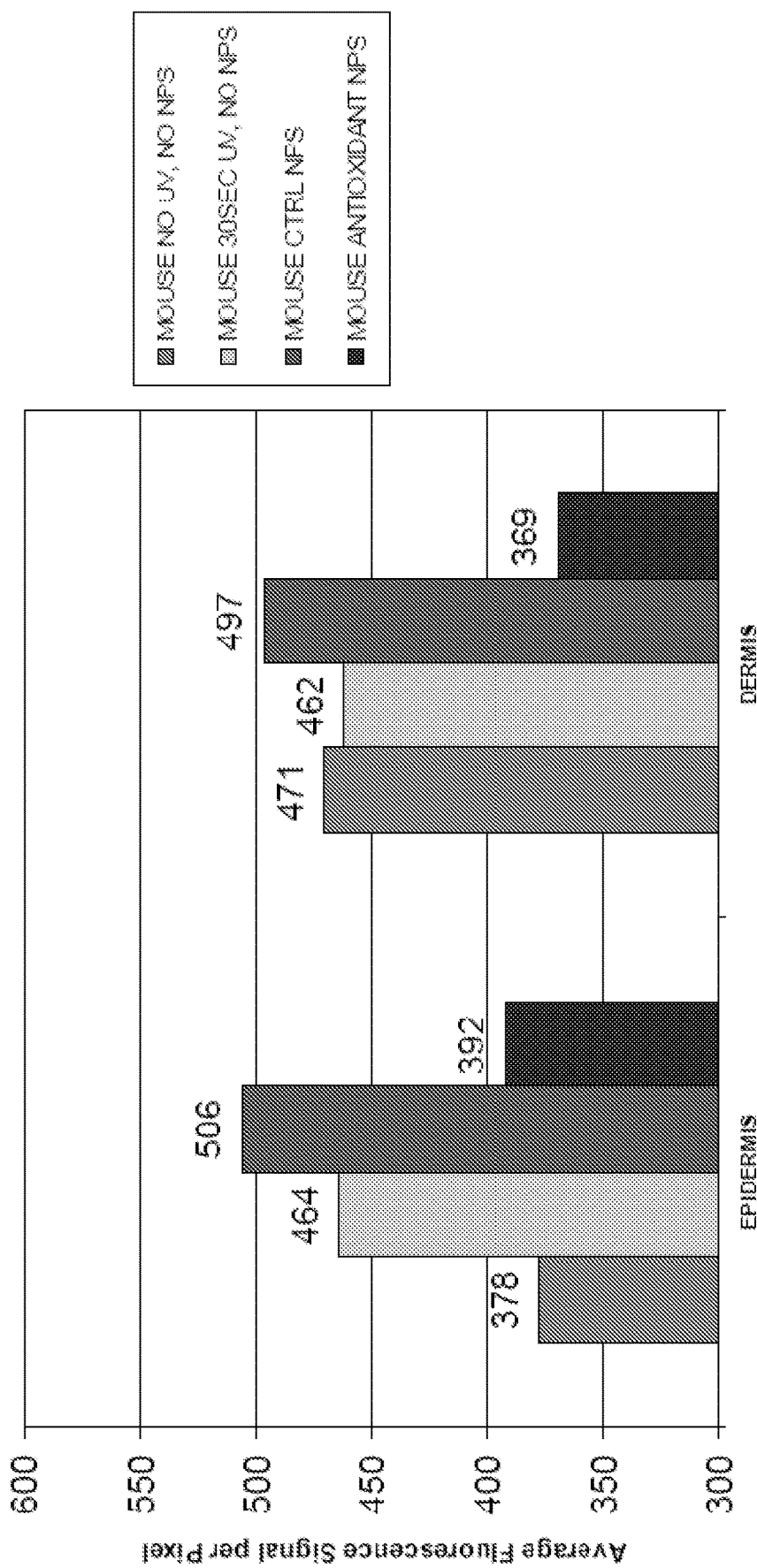

FIGS. 5A and 5B provide graphs of the fluorescence of rat (FIG. 5A) and mouse (FIG. 5B) skin samples treated with control nanoparticles or antioxidant nanoparticles and exposed to UV. FIG. 5C provides a graph of the fluorescence of mouse skin samples treated with control nanoparticles or antioxidant nanoparticles and exposed to UV.

Figure 6A:
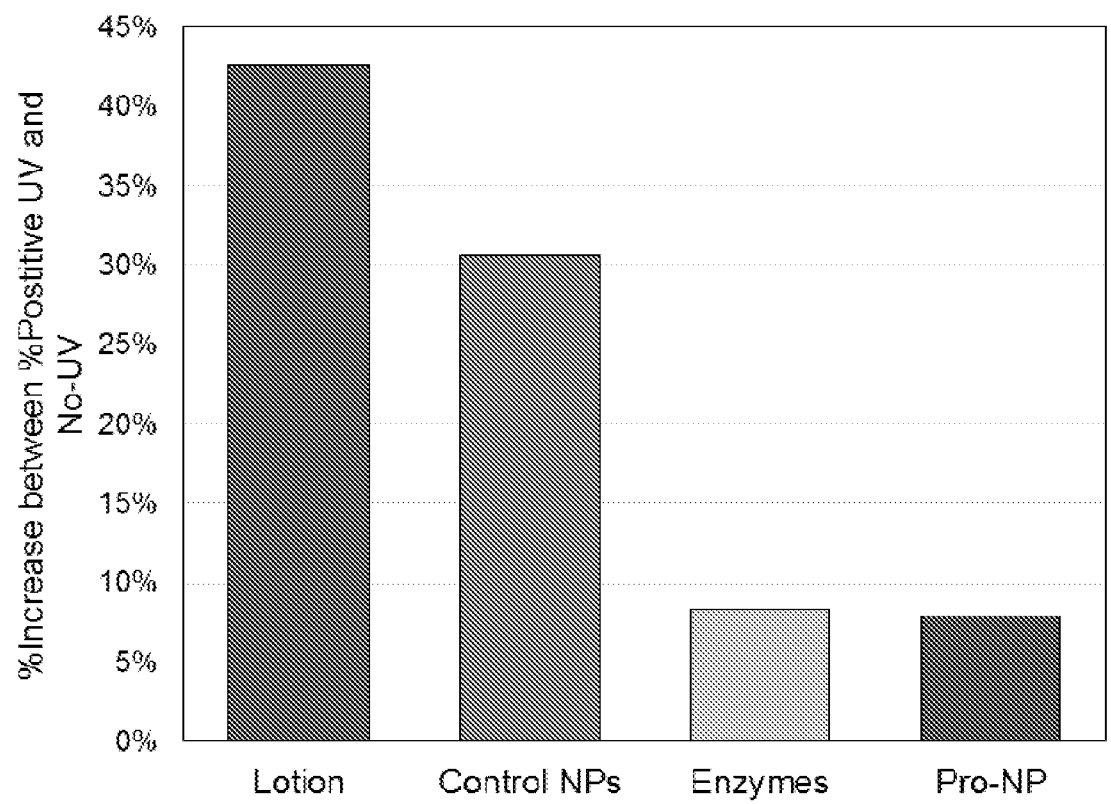
Figure 6B:
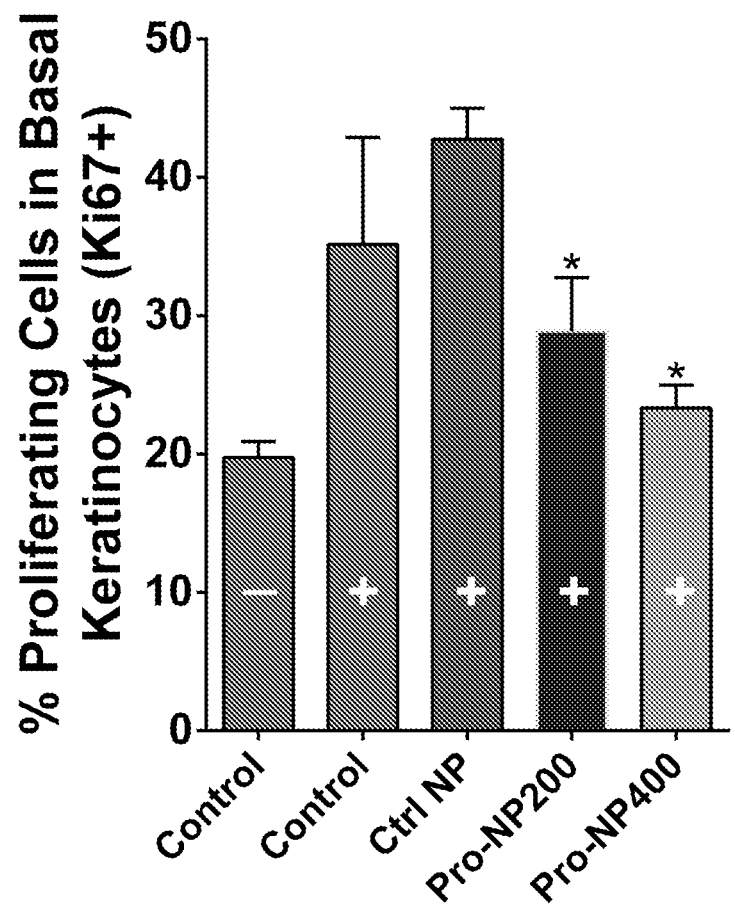
Figure 6C:
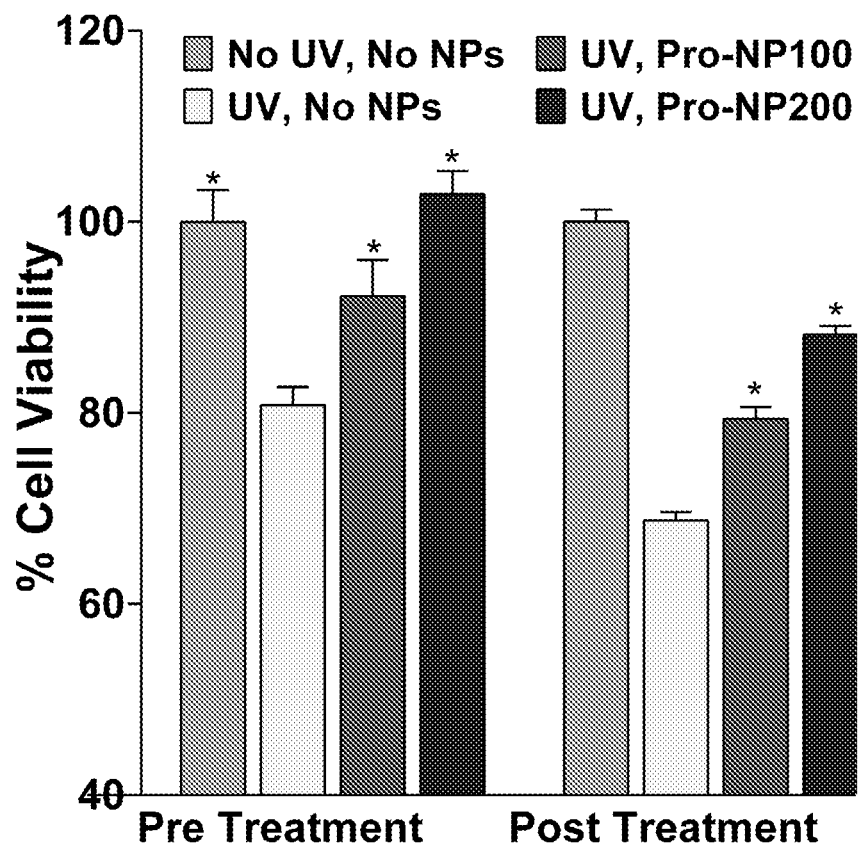
Figure 6D:
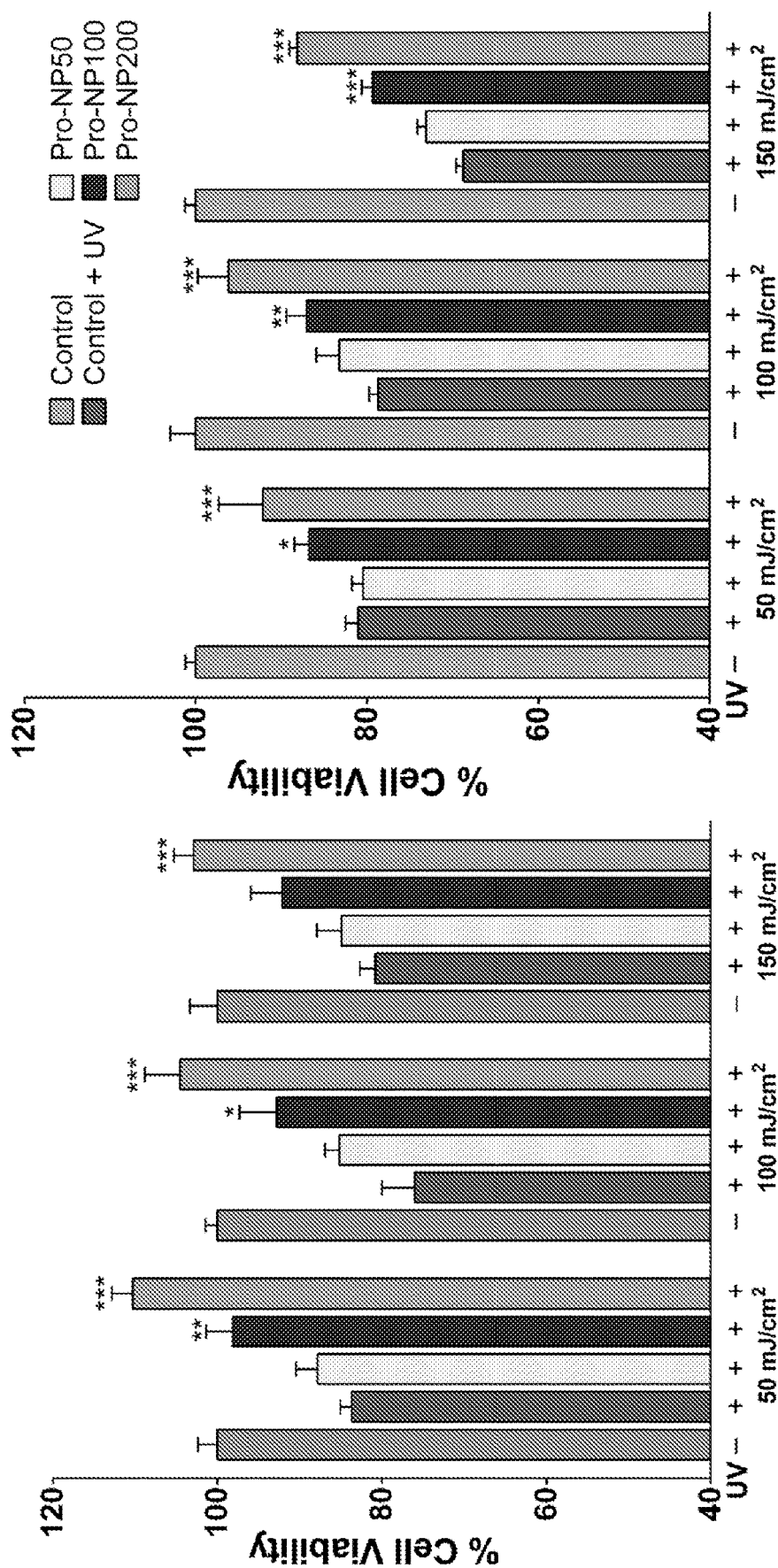
Figure 6E:
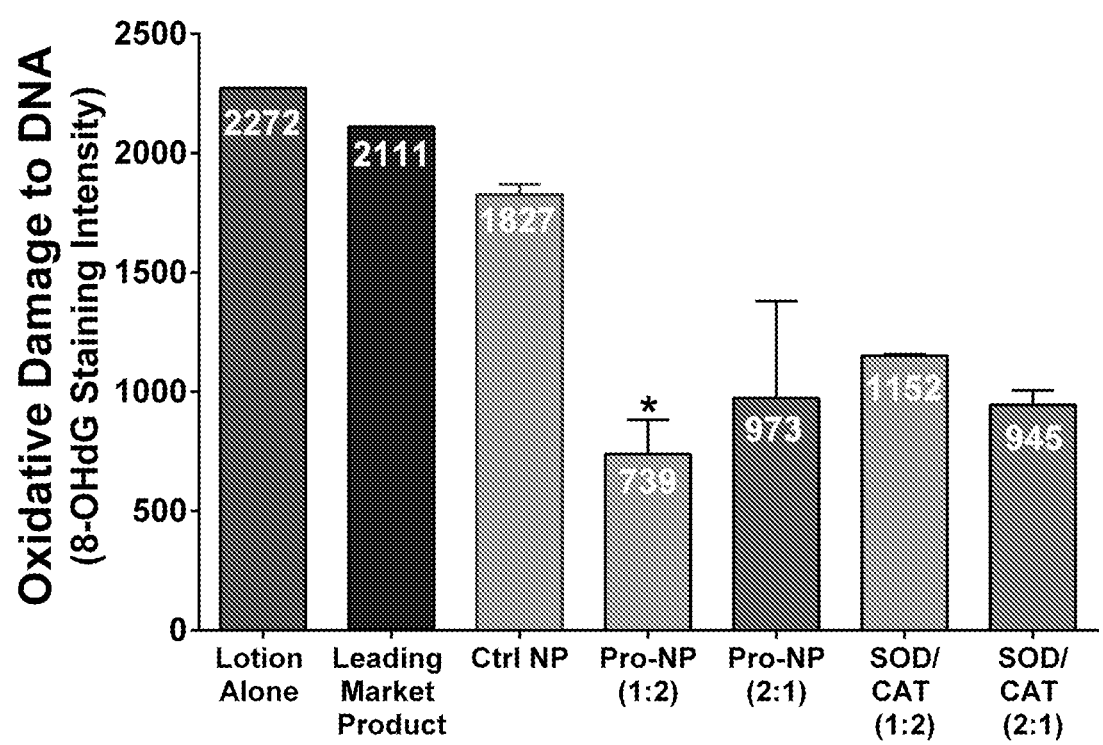

FIG. 6A shows the percent increase in cells positive for thymine dimers after UV exposure compared to before UV exposure. FIG. 6B provides a graph of the Ki-67 positive cells after various treatments. Human skin equivalents were treated overnight on the epidermal surface with indicated treatments (Control nanoparticles (NPs) or Pro-NP™ resuspended in 50 μL PBS), washed and were exposed (+) or unexposed (−) to UV (150 $mJ/cm^2$). Percent Ki-67+ were visualized 24 hours later using immunohistochemical staining in the fixed sections. The average±SD (n=3) of % Ki-67 expressing cells of total keratinocytes (counted in at least 100 total basal keratinocytes) is indicated in the right. *p<0.01 compared to control NP by ANOVA with Dunnet's post-test analysis. FIG. 6C shows that Pro-NP™ blocked UV-induced cell death. HaCaT keratinocytes were treated with different doses of Pro-NP (100 or 200 μg) either 2.5 hours before UV exposure or immediately after UV exposure and cultured for 18 hours before determining cell viability. *P≤0.05 compared to UV exposed vehicle treated group by ANOVA with Dunnet's post-test analysis. FIG. 6D shows that Pro-NP™ blocked UV-induced cell death. HaCaT keratinocytes were treated with different doses of Pro-NP (50, 100, or 200 μg) either 2.5 hours before UV exposure (left) or immediately after UV exposure (right) at various UV intensities (50, 100, or 150 $mJ/cm^2$) and cultured for 18-20 hours before determining cell viability. *P≤0.05 compared to UV exposed vehicle treated group by ANOVA with Dunnet's post-test analysis. FIG. 6E is a graph of oxidative damage to DNA. Human skin equivalents were treated overnight as indicated with NPs or pure proteins mixed in anhydrous lotion (gently rubbed in with a sterile glass rod). Lotions on the surface were removed with a sterile wet cotton swab. The tissues were then exposed to UV (150 $mJ/cm^2$) and cultured for 24 hours before fixing for 8-OHdG immunostaining. Mean fluorescence intensity was quantitated using NIH Image J software. *p<0.01 compared to control NPs by ANOVA with Dunnet's post-test analysis.

Figure 7:
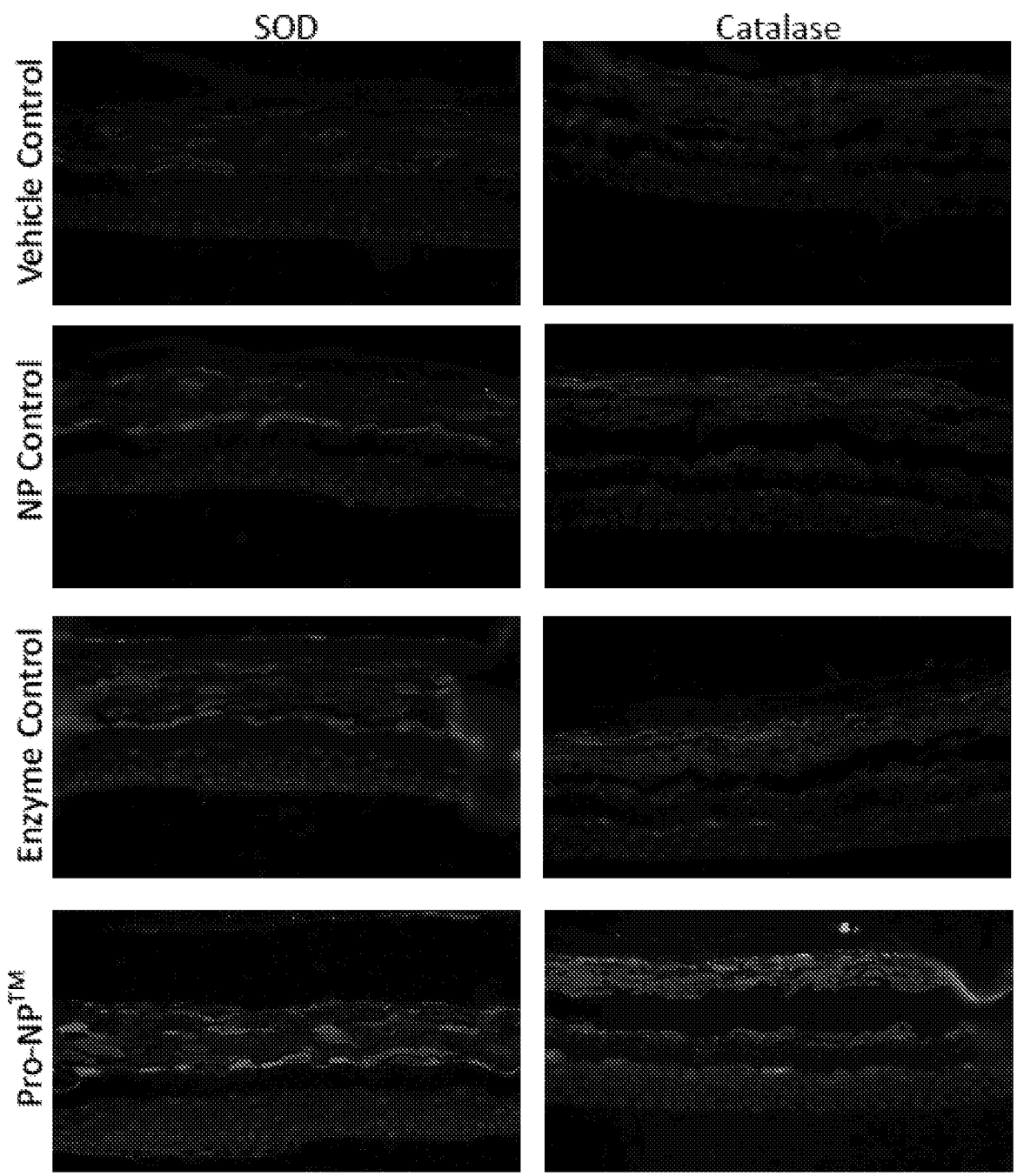

FIG. 7 shows cross section images of artificial human skin epidermis and the extent of penetration of active biomolecules (SOD or catalase)-loaded nanoparticles through skin. Human skin equivalents were treated overnight with pure anhydrous lotion, control nanoparticles, SOD/catalase loaded nanoparticles or pure SOD/catalase mixed in anhydrous lotion (gently rubbed in with a sterile glass rod). Lotions on the surface were removed with a sterile wet cotton swab. The tissues were then cultured for additional 24 hours before fixing and immunostaining. Active SOD and catalase in the skin sections were visualized in the fixed sections using immunofluorescent staining (n=3). The control specimens (lotion alone and control nanoparticles) displayed a lower staining signal for both SOD and catalase throughout the entire skin section. Incubation with pure SOD and catalase mixed in anhydrous lotion showed a slightly higher signal compared to control specimens, but vast majority of the staining was restricted to stratum corneum layers. In contrast, incubation with nanoparticle lotion containing SOD and catalase not only showed higher signal intensity in the upper layers of the skin (stratum corneum), but also produced higher signal intensity in the nucleated epidermal cell layers (nuclei stained with DAPI) for both SOD and catalase.

DETAILED DESCRIPTION OF THE INVENTION

The skin, of course, is not just a flat surface, but is made up of compact layers of cells and connective tissue. The stratum corneum and epidermis is the outer layer and serves as the physical and chemical barrier between the interior body and exterior environment. The dermis is the deeper layer providing the structural support for the skin and is divided into stratum papillare, a loose connective tissue and the reticular layer, which is a denser connective tissue. Finally, below that is the hypodermis, which consists of deposits of fat. The skin's thickness varies with location on the body and the health status of the individual, but the outside layer, the epidermis, is generally around 100 µm or less in thickness (Sandby-Moller et al. (2003) Acta Dermato-Venereol., 83:410-413). The dermis, the next layer in, is generally 1-2 mm thick (Smijs et al. (2011) Nanotechnol. Sci. Appl., 4:95-112; www.lab.anhb.uwa.edu.au/mb140/CorePages/Integumentary/Integum.htm).

It is difficult to generalize about the effectiveness of nanoparticles at penetrating the skin because of wide variations between skin models (in thickness, follicle density, living vs. non-living tissue), variety in types and sizes of nanoparticles, differing methods of application, and different receptiveness of damaged vs. intact skin (Prow et al. (2011) Adv. Drug Deliv. Rev., 63: 470-491). Confocal fluorescence microscopy and other spectroscopic techniques are commonly used to detect and study the penetration of nanoparticles through skin (Zhu et al. (2015) J. Biomed. Opt., 20(5):051006). Microscopy is frequently combined with use of a mechanical sectioning technique called tape stripping, which allows for examination of thin skin layers of progressive depth (Peppelman et al. (2015) Skin Res. Technol., doi:10.1111/srt.12217). However, stripping generally cannot remove any layers deeper than the stratum corneum and the removed layers are of uneven thickness (Touitou et al. (1998) J. Control. Release, 56:7-21). Additionally, the detection of fluorescent dyes in the skin can be confounded by the presence of substantial background autofluorescence over a wide wavelength range (peaks between ~450 and 625 nm) (Na et al. (2000) Skin Res. Technol., 6:112-117).

When working with dermatological applications of nanoparticles, therefore, it would be useful to have a method for imaging fluorescence that (1) was free of interfering background signal, (2) operated on a macro (in millimeters) viewing scale, rather than either a micro or in vivo scale, and (3) also able to quantify the signal intensity. Recent methods reported include techniques, such as Raman spectroscopy, which has been used to quantify the penetration of nanoparticles into skin at micro-scale depths (Belsey et al. (2014) J. Control. Release, 174:37-42; Shah et al. (2012) J. Control. Release, 161:735-745). In this study, a novel, relatively simple, quantifiable imaging method was used to detect and assess the penetration of nanoparticles into and through the epidermis, and even into the dermis. The nanoparticles incorporated a dye that fluoresces in the near-infrared wavelength range and thus avoids interference from the skin's natural autofluorescence. The biodistribution and tumor localization of dye-loaded nanoparticles has been studied as a function of surface charge and size. The incorporated dye provides a high intensity, stable signal at a very low (0.1% w/w) dye loading in nanoparticles in the near-infrared region, the dye and dye-loaded nanoparticles are nontoxic, and can detect as low as 5 µg of nanoparticles (Adjei et al. (2014) Nanomedicine, 9:267-278; Foy et al. (2010) ACS Nano, 4:5217-5224).

Currently, there are many claimed antioxidants contained in skincare products, but none has the characteristics of the nanoparticles of the instant invention (sometimes referred to herein as Pro-NP™), which contain active enzymes naturally used by the body to fight free radicals. Recent research demonstrates the toxic and mutagenic effects of titanium dioxide nanoparticles ($TiO_2$ nanoparticles) when exposed to UV radiation due to photocatalytic activity of $TiO_2$ nanoparticles that generates excessive reactive oxygen species (ROS). The results provided herein show that Pro-NP™ is effective in preventing the damaging effect of ROS. The Pro-NP™ are specially designed to stabilize the antioxidant enzymes, allow their penetration through the skin layers, deliver active enzymes over a sustained period of time, and be completely metabolized by the body in a non-toxic manner. Several studies have shown that naturally occurring antioxidant enzymes that are not packaged and stabilized interact with $TiO_2$ NPs, making them inactive. Natural enzymes are also unstable in biological environments, including when they contact the skin surface due to the presence of proteolytic enzymes or following light or UV exposure or they interact with other ingredients present in the topical lotion or cream. In Pro-NP™, enzymes are encapsulated in polymeric NPs and, hence are stabilized and not directly in contact with $TiO_2$ NPs. The nanoparticles of the instant invention can be used in a variety of skincare products such as lotions, creams, sunscreen, or any other skincare product where it is desirous to prevent development of free radicals, such as upon sun exposure or exposure to environmental factors or toxins, particularly with older individuals whose body's defense mechanisms are deficient. The nanoparticles of the instant invention may be used in other skin conditions where ROS and ROS-mediated inflammation and cell death has been implicated. For example, Rosacea and psoriasis may be caused or exacerbated by excessive levels of ROS and, therefore, can be treated with the nanoparticles of the instant invention.

In accordance with the instant invention, methods of delivering a compound to the skin are provided. The methods of the instant invention comprise administering (particularly topically) at least one nanoparticle of the instant invention (or a composition comprising at least one nanoparticle) comprising or encapsulating the compound to a subject. In a particular embodiment, the method delivers the compound beneath the epidermis and/or dermis, particularly beneath the epidermis to the dermis. In a particular embodiment, the compound is a protein or peptide, particularly a biologically active protein (e.g., enzyme). In certain embodiments, the compound is an antioxidant, particularly an antioxidant enzyme.

In accordance with another aspect of the instant invention, methods of treating, inhibiting, and/or preventing a skin disease or disorder are provided. Examples of skin diseases or disorders include, without limitation: photoaging, sunburn, skin cancer, other UV-radiation related disorders, excess ROS disorders such as Rosacea, and inflammation mediated diseases/disorders such as psoriasis, acne, cold sore, seborrheic eczema, hives, warts, necrotizing fasciitis, cutaneous candidiasis, cellulitis, impetigo, lichen planus, corns, calluses, and shingles. The methods of the instant invention comprise administering (particularly topically) at least one nanoparticle of the instant invention (or a composition comprising at least one nanoparticle) comprising or encapsulating a therapeutic agent for the skin disease or disorder to a subject. In a particular embodiment, the therapeutic agent is a protein or peptide, particularly a biologically active protein (e.g., enzyme). In certain embodiments, the therapeutic agent is an antioxidant, particularly an antioxidant enzyme. The methods may further comprise the administration of at least one other therapeutic agent (e.g., another antioxidant, anti-inflammatory agent, antibacterial agent, cytokine, growth factor) for the treatment, inhibition, or prevention of the skin disease or disorder and regeneration and repair of skin. The additional therapeutic agent (e.g., another antioxidant, anti-inflammatory agent, vitamin, etc.) may be administered in separate composition from the nanoparticles of the instant invention. The compositions may be administered at the same time or at different times (e.g., sequentially). In a particular embodiment, the treatment, inhibition, and/or prevention of a skin disease or disorder occurs due to the reduction of free radical formation (e.g., oxidative stress) in skin by the topical application of nanoparticles containing antioxidant enzymes. In a particular embodiment, the method comprises administering (particularly topically) at least one nanoparticle of the instant invention (or a composition comprising at least one nanoparticle) comprising or encapsulating a therapeutic agent (particularly an antioxidant enzyme) to a subject who has been exposed to $TiO_2$, zinc oxide, or other metal or metal oxide based nanoparticles and UV radiation. In a particular embodiment, the method comprises administering (particularly topically) at least one nanoparticle of the instant invention (or a composition comprising at least one nanoparticle) comprising or encapsulating a therapeutic agent (particularly an antioxidant enzyme) to a subject with $TiO_2$, zinc oxide, or other metal or metal oxide based nanoparticles. For example, the nanoparticles of the instant invention may be administered from about a 5:1 ratio to about a 1:1 ratio (e.g., at about a 2:1 ratio) with metal nanoparticles (e.g., $TiO_2$ nanoparticles).

The nanoparticles of the instant invention may be administered to the subject before, during, and/or after exposure to UV radiation (e.g., exposure to UV levels greater than typical indoor UV levels). In a particular embodiment, the nanoparticles are administered prior to exposure to UV radiation. For example, the nanoparticles may be administered at least 1 minute, 5 minutes, 15 minutes, 30 minutes, 1 hour, 2 hours or more prior to UV exposure, but within a day of exposure to UV exposure (e.g., night treatment). For example, the nanoparticles can provide protection at night when metabolic activity is higher whereas during day time from UV rays and environmental factors, thus providing 24 hour protection. In another embodiment, nanoparticles are applied after the UV exposure to show skin recovery with treatment.

The nanoparticles of the instant invention comprise at least one polymer and at least one encapsulated compound. Generally, the nanoparticle ranges in size from between 1 nm and 1000 nm, particularly between 1 nm and about 350 nm or between 1 nm and about 250 nm. While the instant invention generally describes the use of proteins in the nanoparticles, it is also within the scope of the instant invention to use other therapeutic agents or compounds of interest in the nanoparticles. The compound(s) can be, without limitation, a biological agent, detectable agents (e.g., imaging agents or contrast agents), or therapeutic agent (e.g., antioxidant, growth factors). Such agents or compounds include, without limitation, polypeptides, peptides, glycoproteins, nucleic acids (DNA, RNA, oligonucleotides, plasmids, siRNA, etc.), synthetic and natural drugs, polysaccharides, small molecules, lipids, and the like.

In a particular embodiment, the polymer of the nanoparticles is a biocompatible and biodegradable polymer. The polymer may be a homopolymer or a copolymer. The polymer may be hydrophobic, hydrophilic, or amphiphilic. If the polymer is a copolymer, it may be a diblock, triblock, or multiblock copolymer. In a particular embodiment, the segments of the block copolymer comprise about 10 to about 500 repeating units, about 20 to about 300 repeating units, about 20 to about 250 repeating units, about 20 to about 200 repeating units, or about 20 to about 100 repeating units. Suitable polymers include, without limitation: poly(lactide-co-glycolides), poly(lactic acid), poly(alkylene glycol), polybutylcyanoacrylate, poly(methylmethacrylate-co-methacrylic acid), poly-allylamine, polyanhydride, polyhydroxybutyric acid, polyorthoesters, and the like. In particular embodiments, a nanoparticle is composed of a copolymer comprising at least one poly(lactic acid) segment and at least one poly(glycolic acid) segment. In a particular embodiment, the polymer is poly (lactide-co-glycolide) (PLGA). Examples of biocompatible polymers include, without limitation: natural or synthetic polymers such as polystyrene, polylactic acid, polyketal, butadiene styrene, styreneacrylicvinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly(lactic-co-glycolic acid), and the like. Examples of natural polymers include polypeptides including those modified non-peptide components, such as saccharide chains and lipids; nucleotides; sugar-based biopolymers such as polysaccharides; cellulose; carbohydrates and starches; dextrans; lignins; polyamino acids; adhesion proteins; lipids and phospholipids (e.g., phosphorylcholine).

The nanoparticles of the present invention can further contain a polymer that affects the charge or lipophilicity or hydrophilicity of the particle. Any biocompatible polymer can be used for this purpose, including but not limited to, poly(vinyl alcohol).

The nanoparticles of the present invention can further comprise a plasticizer. The plasticizer may facilitate sustained release of the encapsulated compound by maintaining the structure of the nanoparticle. A plasticizer may be added to the nanoparticles to maintain the glass transition temperature above 37° C. despite a decline in molecular weight of the polymer with time. Without being bound by theory, the addition of the plasticizer allows for pores in the nanoparticle to remain open and facilitate a continuous release of the encapsulated compound. Suitable plasticizers are generally inert, non-toxic, and biocompatible. Plasticizers include, without limitation, triethyl citrate (e.g., Citroflex®, Morflex Inc., Greensboro, N.C.), glyceryl triacetate (e.g., triacetin), L-tartaric acid dimethyl ester (dimethyl tartrate, DMT), benzoates (e.g. terephthalates such as dioctyl terephthalate/DEHT,1,2-cyclohexane dicarboxylic acid diisononyl ester (Hexamoll® DINCH®), epoxidized vegetable oils, alkyl sulphonic acid phenyl ester (ASE), sulfonamides (e.g. N-ethyl toluene sulfonamide (o/p ETSA), ortho and para isomers, N-(2-hydroxypropyl) benzene sulfonamide (HP BSA), N-(n-butyl) benzene sulfonamide (BBSA-NBBS)), organophosphates (e.g., tricresyl phosphate (TCP), tributyl phosphate (TBP)), glycols/polyethers, triethylene glycol (e.g., dihexanoate (3G6, 3GH), tetraethylene glycol diheptanoate (4G7)), polymeric plasticizer (e.g. polybutene), and bio-based plasticizers. Bio-based plasticizers may have better biodegradability and fewer biochemical effects and include, without limitation: acetylated monoglycerides, alkyl citrates, triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), andrimethyl citrate (TMC). In a particular embodiment, the nanoparticles comprise the plasticizer dimethyl tartrate (DMT). The amount of plasticizer employed in a nanoparticle can range from about 5 to about 40 weight percent of the nanoparticle, particularly from about 10 to 20 weight percent of the nanoparticle. In particular embodiments, the plasticizer encompasses about 10 weight percent of the nanoparticle.

The nanoparticles of the instant invention may also comprise a surfactant (e.g. polyvinyl alcohol) to facilitate their dispersion and stability in the topical formulation. These surface-associated surfactants/emulsifier can be anionic (e.g., sodium dodecyl sulfate, sodium dodecyl benzene sulfonate, sodium laureth sulfate, sodium lauroyl sarcosinate, sodium myreth sulfate, sodium pareth sulfate, sodium stearate, etc.), neutral (e.g., ethoxylated aliphatic alcohol, polyoxyethylene surfactants, carboxylic esters, polyethylene glycol esters, anhydrosorbitol ester and ethoxylated derivatives thereof, glycol esters of fatty acids, carboxylic amides, monoalkanolamine condensates, polyoxyethylene fatty acid amides), or cationic (e.g., quaternary ammonium salts, amines with amide linkages, polyoxyethylene alkyl and alicyclic amines, N,N,N',N' tetrakis substituted ethylenediamines, 2-alkyl 1-hydroxethyl 2-imidazolines); amphoteric type (e.g., amphoteric surfactants contains both an acidic and a basic hydrophilic moiety in their surface, N-coco 3-aminopropionic acid/sodium salt, N-tallow 3-iminodipropionate disodium salt, N-carboxymethyl N dimethyl N-9 octadecenyl ammonium hydroxide, N-cocoamidethyl-N-hydroxyethylglycine sodium salt.

As stated hereinabove, the nanoparticle of the instant invention comprises a compound (e.g., therapeutic agent) covered or coated by the polymer. In a particular embodiment, the compound is a protein or peptide, particularly a biologically active protein (e.g., enzyme). In certain embodiments, the compound is an antioxidant, particularly an antioxidant enzyme. Antioxidants which can be formulated in a nanoparticle of the present invention include, without limitation, antioxidant enzymes, small molecule antioxidants, natural and synthetic, or combinations thereof. Antioxidants are substances which neutralize the activity of reactive oxygen species or inhibit the cellular damage done by the reactive species or their reactive byproducts or metabolites. The term "antioxidant" may also refer to compounds that inhibit, prevent, reduce or ameliorate oxidative reactions or compounds that inhibit reactions promoted by reactive oxygen species such as oxygen itself, oxygen free radicals, or peroxides. Examples of antioxidant enzymes include, but are not limited to: superoxide dismutase (e.g., SOD1), catalase, peroxidase, glutathione peroxidase, glutathione reductase, glutathione-S-transferase, and hemeoxygenase. For example, the antioxidant enzyme superoxide dismutase (SOD), particularly, SOD1 (also called Cu/Zn SOD), is known to catalyze the dismutation of superoxide ($O_2.^-$). Examples of other antioxidants include, without limitation: plant derived antioxidants, vitamin E, vitamin C, ascorbyl palmitate, vitamin A, carotenoids, beta carotene, retinoids, xanthophylls, lutein, zeaxanthin, flavones, isoflavones, flavanones, flavonols, catechins, ginkgolides, anthocyanidins, proanthocyanidins, carnosol, carnosic acid, organosulfur compounds, allylcysteine, alliin, allicin, lipoic acid, omega-3 fatty acids, eicosapentaeneoic acid (EPA), docosahexaeneoic acid (DHA), tryptophan, arginine, isothiocyanates, quinones, ubiquinols, butylated hydroxytoluene (BHT), butylated hydroxyanisole (BHA), super-oxide dismutase mimetic (SODm), and coenzymes-Q. In a particular embodiment, the antioxidant is an antioxidant vitamin (e.g., Vitamin A, C, and/or E). In a particular embodiment, the antioxidant is an antioxidant enzyme, particularly superoxide dismutase or catalase (e.g., of mammalian, particularly human, origin). The antioxidant may be isolated from natural sources or prepared recombinantly.

The nanoparticles of the instant invention may be synthesized by known methods. Methods for synthesizing nanoparticles are provided in U.S. Pat. No. 7,332,159; Adjei et al. (2014) Nanomedicine, 9:267-278; Singhal et al. (2013) Cell Death Dis., 4:e903; and Reddy et al. (2009) FASEB J., 23(5):1384-1395. In a particular embodiment, the nanoparticles of the instant invention are synthesized by an emulsion solvent evaporation method. The nanoparticles may also be purified after synthesis by methods known in the art. For example, the nanoparticles may be purified by size exclusion chromatography (e.g., using a Sephacryl™ column) and/or centrifugal filtration (e.g., using a molecular weight cutoff filter). In a particular embodiment, the nanoparticles are purified such that at least 95%, 96%, 97%, 98%, 99%, or more of undesired components are removed from the sample.

In a particular embodiment of the instant invention, the nanoparticles of the instant invention are a mixture of SOD containing nanoparticles and catalase containing nanoparticles. In a particular embodiment, the w/w ratio of SOD nanoparticles to catalase nanoparticles is from about 1:10 to about 3:1, particularly about 1:5 to about 1:1, particularly about 1:2. The amount of nanoparticles may also be defined by the activity of the antioxidant enzymes. In a particular embodiment, one mg of the nanoparticles of the instant invention comprise about 10 to about 500 active units, particularly about 50 to about 250 active units, particularly about 125 active units of SOD and about 5 to about 200 active units, particularly about 40 to about 150 active units, particularly about 90 active units of catalase. The nanoparticles of the instant invention may be delivered to a subject at various concentrations. In a particular embodiment, the nanoparticles are delivered to a subject at a concentration up to about 1000 µg/ml, up to about 800 µg/ml, or up to about 600 µg/ml.

In accordance with another aspect of the instant invention, compositions comprising the nanoparticles of the instant invention are provided. In a particular embodiment, the composition is a topical composition (for application to the skin). The compositions of the instant invention comprise at least one nanoparticle and at least one carrier (e.g., a carrier acceptable for topical delivery (e.g., a carrier acceptable for skin application; e.g., a pharmaceutically and/or cosmetically acceptable carrier). The topical compositions of the present invention may be made into a wide variety of product types such as, without limitation, liquids, lotions, powders, creams, salves, gels, foams, milky lotions, sticks, sprays (e.g., pump spray), aerosols, ointments, pastes, mousses, dermal patches, adhesives (e.g., adhesive tape), bandages, pad, scaffold, nanofibers, films, cleansing agent, controlled release devices, and other equivalent forms. In a particular embodiment, the composition is a sunscreen. In a particular embodiment, the composition is a lotion or cream product.

Acceptable carriers can be, without limitation, sterile liquids, such as water (may be deionized), alcohol (e.g., ethanol, isopropanol, benzyl alcohol), oils (including those of petroleum, animal, vegetable or synthetic origin, such as peanut oil, soybean oil, mineral oil, sesame oil and the like), and other organic compounds or copolymers. Water or aqueous saline solutions and aqueous dextrose and glycerol solutions may also be employed as carriers. Suitable carriers and other agents of the compositions of the instant invention are described in "Remington's Pharmaceutical Sciences" by E. W. Martin (Mack Pub. Co., Easton, Pa.) and "Remington: The Science and Practice of Pharmacy" by Alfonso R. Gennaro (Lippincott Williams & Wilkins) (each of the foregoing references being incorporated herein by reference). Additional general types of acceptable topical carriers include, without limitation, emulsions (e.g., microemulsions and nanoemulsions), gels (e.g., an aqueous, alcohol, alcohol/water, or oil (e.g., mineral oil) gel using at least one suitable gelling agent (e.g., natural gums, acrylic acid and acrylate polymers and copolymers, cellulose derivatives (e.g., hydroxymethyl cellulose and hydroxypropyl cellulose), and hydrogenated butylene/ethylene/styrene and hydrogenated ethylene/propylene/styrene copolymers), solids (e.g., a wax-based stick, soap bar composition), or powder (e.g., bases such as talc, lactose, starch, and the like), spray, and liposomes (e.g., unilamellar, multilamellar, and paucilamellar liposomes, optionally containing phospholipids). The acceptable carriers also include stabilizers, penetration enhancers, chelating agents (e.g., EDTA, EDTA derivatives (e.g., disodium EDTA and dipotassium EDTA), iniferine, lactoferrin, and citric acid), and excipients. Protocols and procedures which facilitate formulation of the topical compositions of the invention can be found, for example, in Cosmetic Bench Reference (Cosmetics & Toiletries, Allured Publishing Corporation, Illinois) and in International Cosmetic Ingredient Dictionary and Handbook ($15^{th}$ Ed.) (each of the foregoing references being incorporated herein by reference).

The topical composition of the instant invention may be aqueous or anhydrous. In a particular embodiment, the composition is anhydrous. In a particular embodiment, the composition is silicone-based (e.g., comprising polysilicone-11 and/or cyclopentasiloxane (e.g., gransil GCM-5)). In a particular embodiment, the topical composition comprises from about 0.001% to about 1.0% nanoparticles, particularly about 0.005 to 0.5% nanoparticles (e.g., by weight).

As stated hereinabove, the compositions of the instant invention may further comprise at least one other agent (e.g., therapeutic agent) in addition to the nanoparticles. Alternatively, the other agent (e.g., therapeutic agent) may be contained within another separate composition from the nanoparticles of the instant invention. The compositions may be administered at the same time or at different times (e.g., sequentially). In a particular embodiment, to achieve sequential delivery, the product can be developed in the form of layers (e.g., in bandage or scaffold). Additional agents (e.g., therapeutic agents) that may be included in the compositions of the instant invention include, without limitation: antioxidants (e.g., small molecule or proteins), vitamins, skin supplements, oils, triglycerides, unsaturated fatty acids, antibacterial agents (e.g., antibiotics), anti-infective agents (e.g., retinoic acid), and extracellular matrix agents (e.g., collagen or hyaluronic acid). The agents may be incorporated in oil phase or water phase or in both (e.g., of a topical cream or lotion).

These nanoparticles may be employed therapeutically under the guidance of a physician or other healthcare professional or self-administered by the subject/patient. The pharmaceutical preparation comprising the nanoparticles of the invention may be conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of nanoparticles in the chosen medium may depend on the hydrophobic or hydrophilic nature of the medium, as well as the size, enzyme activity, and other properties of the nanoparticles. Solubility limits may be easily determined by one skilled in the art.

As used herein, "acceptable medium" or "carrier" includes any and all solvents, dispersion media and the like which may be appropriate for the desired route of administration of the preparation, as exemplified in the preceding discussion. In a particular embodiment, the carrier is for topical application and is a pharmaceutically acceptable carrier or a cosmetically acceptable carrier. The use of such media for active substances is known in the art. Except insofar as any conventional media or agent is incompatible with the nanoparticles to be administered, its use in the pharmaceutical preparation is contemplated.

The dose and dosage regimen of a nanoparticle according to the invention that is suitable for administration to a particular subject may be varied considering the patient's age, sex, weight, general medical condition, and the specific condition for which the nanoparticle is being administered and the severity thereof. The route of administration of the nanoparticle, the pharmaceutical carrier with which the nanoparticle is combined, and the nanoparticle's biological activity may also be considered.

Selection of a suitable pharmaceutical preparation may also depend upon the mode of administration chosen. For example, the nanoparticles of the invention may be administered topically. In these instances, the pharmaceutical preparation comprises the nanoparticles dispersed in a medium that is compatible with the site of administration (e.g., skin). In a particular embodiment, the nanoparticles may also be injected into skin layers either using needle or diffused through the skin layers using ultrasound/UV rays/permeability enhancers or physical and mechanical techniques. As explained hereinabove, pharmaceutical preparations for topical administration are known in the art. The lipophilicity of the nanoparticles or the pharmaceutical preparation in which they are delivered may be increased so that the molecules can arrive at their target location. Methods for increasing the lipophilicity of a molecule are known in the art.

Pharmaceutical compositions containing a nanoparticle of the present invention as the active ingredient in intimate admixture with a pharmaceutical carrier can be prepared according to conventional pharmaceutical compounding techniques. The carrier may take a wide variety of forms depending on the form of preparation desired for administration, e.g., topically. A pharmaceutical preparation of the invention may be formulated in dosage unit form for ease of administration and uniformity of dosage. Dosage unit form, as used herein, refers to a physically discrete unit of the composition appropriate for the subject using the nanoparticles of the instant invention. Each dosage should contain a quantity of active ingredient calculated to produce the desired effect in association with the selected carrier. Procedures for determining the appropriate dosage unit are well known to those skilled in the art. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules in animal models. Various concentrations of nanoparticle pharmaceutical preparations may be administered to mice or other mammals, and the minimal and maximal dosages may be determined based on the beneficial results and side effects observed as a result of the treatment. Appropriate dosage unit may also be determined by assessing the efficacy of the nanoparticles treatment in combination with other standard drugs. The dosage units of nanoparticles may be determined individually or in combination with each treatment according to the effect detected.

The pharmaceutical preparation comprising the nanoparticles may be administered at appropriate intervals, for example, at least twice a day or more until the pathological symptoms are reduced or alleviated, after which the dosage may be reduced to a maintenance level. The appropriate interval in a particular case would normally depend on the condition of the patient. The preparation may also be administered "as needed" (e.g., prior to exposure to UV radiation).

Definitions

The following definitions are provided to facilitate an understanding of the present invention:

The singular forms "a," "an," and "the" include plural referents unless the context clearly dictates otherwise.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition resulting in a decrease in the probability that the subject will develop the condition.

As used herein, the term "subject" refers to an animal, particularly a mammal, particularly a human.

A "therapeutically effective amount" of a compound or a pharmaceutical composition refers to an amount effective to prevent, inhibit, treat, or lessen the symptoms of a particular disorder or disease. The treatment of inflammation or infection herein may refer to curing, relieving, and/or preventing the inflammation or infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Polysorbate 80), emulsifier, buffer (e.g., Tris HCl, acetate, phosphate), bulking substance (e.g., lactose, mannitol), excipient, auxilliary agent or vehicle with which an active agent of the present invention is administered. Pharmaceutically or cosmetically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

As used herein, the term "purified" or "to purify" refers to the removal of contaminants or undesired compounds from a sample or composition. For example, purification can result in the removal of from about 70 to 90%, up to 100%, of the contaminants or undesired compounds from a sample or composition. In certain embodiments, at least 90%, 93%, 95%, 96%, 97%, 98%, 99%, 99.5%, or more of undesired compounds from a sample or composition are removed from a preparation.

As used herein, the term "antioxidant" refers to compounds that neutralize the activity of reactive oxygen species or inhibit the cellular damage done by the reactive species or their reactive byproducts or metabolites. The term "antioxidant" may also refer to compounds that inhibit, prevent, reduce or ameliorate oxidative reactions. Examples of antioxidants include, without limitation, antioxidant enzymes (e.g., superoxide dismutase, catalase, or peroxidases such as glutathione peroxidase), animal or plant derived antioxidants, vitamin E, vitamin C, ascorbyl palmitate, vitamin A, carotenoids, beta carotene, retinoids, xanthophylls, lutein, zeaxanthin, flavones, isoflavones, flavanones, flavonols, catechins, ginkgolides, anthocyanidins, proanthocyanidins, carnosol, carnosic acid, organosulfur compounds, allylcysteine, alliin, allicin, lipoic acid, omega-3 fatty acids, eicosapentaeneoic acid (EPA), docosahexaeneoic acid (DHA), tryptophan, arginine, isothiocyanates, quinones, ubiquinols, butylated hydroxytoluene (BHT), butylated hydroxyanisole (BHA), super-oxide dismutase mimetic (SODm), and coenzymes-Q.

The terms "reactive oxygen species," or "oxidative species," as used herein, refer to oxygen derivatives from oxygen metabolism or the transfer of electrons, resulting in the formation of "free radicals" (e.g., superoxide anion or hydroxyl radicals).

As used herein, the term "photoaging" refers to skin damage due to exposure, particularly prolonged or accumulative exposure, to ultraviolet (UV) radiation. Examples of symptoms of photoaging include, without limitation: dyspigmentation, wrinkles, telangiectasias (spider veins), solar lentigines (age spots), actinic keratoses, and cutaneous malignancies.

As used herein, the term "sunscreen" includes compositions for topical application to sun-exposed areas of the skin and/or hair of mammals, especially humans. Sunscreens may comprise one or more chemical sunblocks (e.g., para-aminobenzoic acid (PABA) and derivatives thereof, benzophenones, cinnamates and esters thereof, salicylates, metal oxides (e.g., titanium dioxide and zinc oxide), padimate O (OD-PABA, octyldimethyl-PABA, σ-PABA), phenylbenzimidazole sulfonic acid (Ensulizole, Eusolex 232, PBSA, Parsol HS), cinoxate (2-ethoxyethyl p-methoxycinnamate), dioxybenzone (benzophenone-8), oxybenzone (benzophenone-3, Eusolex 4360, Escalol 567), homosalate (homomethyl salicylate, HMS), menthyl anthranilate (meradimate), octocrylene (Eusolex OCR, 2-cyano-3,3-diphenyl acrylic acid, 2-ethylhexylester), octyl methoxycinnamate (octinoxate, EMC, OMC, Ethylhexyl methoxycinnamate, Escalol 557, 2-ethylhexyl-paramethoxycinnamate, Parsol MCX), octyl salicylate (octisalate, 2-ethylhexyl salicylate, Escalol 587), sulisobenzone (2-hydroxy-4-methoxybenzophenone-5-sulfonic acid, 3-benzoyl-4-hydroxy-6-methoxybenzene-sulfonic acid, benzophenone-4, Escalol 577), trolamine salicylate (triethanolamine salicylate), avobenzone 1-(4-methoxyphenyl)-3-(4-tert-butylphenyl)propane-1,3-dione, butyl methoxy dibenzoylmethane, BMDBM, Parsol 1789, Eusolex 9020), ecamsule (mexoryl SX, terephthalylidene dicamphor sulfonic acid), 4-methylbenzylidene camphor (Enzacamene, Parsol 5000, Eusolex 6300, MBC), tinosorb M (bisoctrizole, methylene bis-benzotriazolyl tetramethylbutylphenol, MBBT); tinosorb S (bis-ethylhexyloxyphenol methoxyphenol triazine, bemotrizinol, BEMT, anisotriazine) tinosorb A2B (tris-biphenyl triazine), neo heliopan AP (bisdisulizole disodium, disodium phenyl dibenzimidazole tetrasulfonate, bisimidazylate, DPDT), mexoryl XL (drometrizole trisiloxane), benzophenone-9 (Uvinul DS 49, CAS 3121-60-6, sodium dihydroxy dimethoxy disulfobenzophenone); Uvinul T 150 (octyl triazone, ethylhexyl triazone, EHT); Uvinul A Plus (diethylamino hydroxybenzoyl hexyl benzoate); Uvasorb HEB (iscotrizinol, diethylhexyl butamido triazone, DBT); Parsol SLX (dimethico-diethylbenzalmalonate, polysilicone-15), amiloxate (isopentyl-4-methoxycinnamate, isoamyl p-Methoxycinnamate, IMC, neo heliopan E1000).

The following examples provide illustrative methods of practicing the instant invention, and are not intended to limit the scope of the invention in any way.

Example 1

Materials and Methods
Materials
Poly(D,L-lactic-co-glycolic acid) (PLGA) with an inherent viscosity of 0.95-1.20 was purchased from Durect Corporation (Cupertino, Calif. Near-infrared (NIR) dye (SDB 5491) was purchased from H.W. Sands Corporation (Jupiter, Fla.). Polyvinyl alcohol (PVA) was purchased from Sigma-Aldrich (St. Louis, Mo.). Human cadaver skin was obtained from the Anatomy Gifts Registry (Hanover, Md.).
Formulation of Nanoparticles
Nanoparticles were formulated by an emulsion solvent evaporation method (Adjei et al. (2014) Nanomedicine, 9:267-278). In brief, a polymer solution of 90 mg PLGA and 100 µg of near-infrared dye in 3 ml chloroform was emulsified into 18 ml of 2% w/v PVA solution using a stepped microtip probe for a total time of six minutes on a Misonix Sonicator® XL (Qsonica, Newtown, Conn.), and then processed for five minutes at 5000 psi with an EmulsiFlex®-05 high-pressure homogenizer (Avestin, Ottawa, ON). The emulsion was stirred overnight in a fume hood with a face velocity of 210 ft/min (6400 cm/min), followed by one hour of stirring in a vacuum desiccator, in order to completely evaporate the chloroform. The nanoparticles were washed by ultracentrifugation, three times for 30 min at 30,000 RPM (82,000×g), in an Optima™ XE-90 with a 50.2 Ti rotor (Beckman Coulter, Brea, Calif.), and resuspended after each centrifugation with autoclaved Milli-Q® water (ASTM Type 1 water, produced by the EMD Millipore Super-Q® Plus filtration system; EMD Millipore, Darmstadt, Germany). They were sonicated as above for two minutes after each resuspension. After a final centrifugation at 4000 RPM (2000×g) for 10 min in a Thermo Electron Sorvall® Legend® RT Plus centrifuge (Thermo Scientific, Waltham, Mass.), the supernatant was frozen and then lyophilized in a FreeZone® 4.5 (Labconco, Kansas City, Mo.) for 48 hours in a 1% sucrose solution to minimize particle aggregation during lyophilization.
Characterization of Nanoparticles
Nanoparticle size and zeta potential were determined by dynamic light scattering with the NICOMP™ 380 ZLS (Particle Sizing Systems, Port Richey, Fla.). Measurements were made on a nanoparticle suspension of approximately 0.2 mg nanoparticles/mL of water. Nanoparticles were tested for release of the incorporated dye in phosphate-buffered saline (PBS) with 1% bovine serum albumin to maintain sink condition. For this test, 2 mg of nanoparticles suspended in 1 mL of this buffer was dialyzed against 5 mL of the same buffer in a 1 mL Float-A-Lyzer® with 0.5 kD cut-off (Spectrum Laboratories, Rancho Dominguez, Calif.). Buffer was collected and replaced at predetermined time points for four days, and the fluorescence signal from the samples was captured and quantified using a near-infrared filter on the Maestro™ in vivo fluorescence imaging system (Model: Maestro™ EX 3.0, PerkinElmer, Waltham, Mass.), as described in detail below. Release sample readings were compared to those of a standard plot from a series of dilutions (1-200 ng) of dye in the same buffer. Dye stock solution was prepared in ethanol at a concentration of 2.5-50 µg/mL.

Permeation Studies Through the Skin Layers

Lyophilized nanoparticles were mixed into a commercially available oil-in-water skin cream (2-3 mg of particles to approximately 50 mg of commercially available dry skin cream) and applied gently with a small stainless steel spatula to the entire epidermal surface of each skin specimen. Cream ingredients were water/agua, mineral oil, isopropyl palmitate, petrolatum, glycerin, steric acid, ceresin, glyceryl stearate, cetyl alcohol, sorbitan oleate, candela wax, triethanolamine, laureth-23, fragrance, preservatives, and chelating agents. Control specimens received only the cream. Skin samples were frozen when received, and measured at least 8×8 inches in epidermal surface area. Thickness skin samples ranged from five to ten millimeters. Individual specimens, approximately 15 mm long×5 mm wide, were cut from these large samples with a new #10 disposable scalpel (Fisher Scientific, Waltham, Mass.). Contiguous pairs of specimens were matched as treated and control specimens for each trial. The skin specimens were thawed to room temperature before cream was applied to their epidermal surface with extra care to ensure that no cream touched the sides of the specimens. The specimens were then placed with epidermal side facing the top in individual wells of a sterile 6-well tissue culture plate (Corning Inc., Corning, N.Y.) and 50 µL of Milli-Q® water was pipetted at the bottom of each specimen to prevent drying of the tissue. The water in the plate did not come in contact with the epidermal layer but sufficient enough to keep the tissue hydrated. Plates were covered with a lid, wrapped in foil, and incubated for either 3 hours or 24 hours, in a Labnet 311DS incubator (Labnet International, Edison, N.J.) maintained at a temperature of 32° C. to simulate normal body temperature at the surface of the skin (Campbell et al. (2012) J. Control. Release, 162:201-207). After incubation, the cream was removed with consistent motions of a lint-free laboratory tissue (Kimberly-Clark, Irving, Tex.) on each specimen and specimens were handled only with sanitized tongs that did not touch the epidermal surface, so that no cream touched the cut sides of the specimen as it was removed. Each pair of specimens was mounted between glass microscope slides in a package that compressed the samples uniformly and held them stably in place for imaging on both sides. Specimens were not moved once placed into position on a slide, to prevent spreading of any cream or nanoparticles from the surface to the sides of the specimens.

To ensure that the signal seen was due to penetration of nanoparticles themselves and not from dye that might have been released from nanoparticles in the cream and diffused through the skin, cream containing nanoparticles was applied over dialysis membrane with a molecular weight cut-off of approximately 14 kDa (Sigma-Aldrich), which was placed on top of skin specimens. Released dye could diffuse through the dialysis membrane but nanoparticles would remain on top of it. These specimens were also mounted between glass slides for imaging as described above.

Imaging

The Maestro™ imaging system was used to obtain images of each specimen from both sides to quantify the NIR signal of nanoparticles due to their penetration through the skin layers. The system recorded fluorescence signal using two filter sets, blue to acquire wavelengths from 500 nm to 720 nm (excitation wavelength=455 nm) and near-infrared to acquire wavelengths from 740 nm to 950 nm (excitation wavelength=704 nm). With the imaging system, it is possible to move the sample stage up and down to adjust the position of the sample with respect to the lens. Here, the imaging was at stage 2C level. Signals were acquired in 10 nm increments through the specified range, with a 1000 ms exposure time at each wavelength. Specimens exhibited background autofluorescence with an emission peak at 550 nm, and the near-infrared dye displayed an emission peak at 780 nm. The Maestro™ system separated and quantified those signals for comparison between treated and control specimens, and between different regions of each specimen.

Results

The particles had a mean diameter of approximately 165 nm with a polydispersity index of 0.135 (FIG. 1A). The release of dye in 1% bovine serum albumin (BSA) solution in PBS was less than 10% in 96 hours, with about 2% release occurring in 3 hours and 7% in 24 hours (FIG. 1B). In the testing of dye release in commercial oil-in-water skin cream, treated specimens where dialysis membrane was placed between the skin and sample, showed no greater near-infrared fluorescence than did control specimens, indicating that there was no release of dye into the cream and, hence, the signal seen through the skin layers is due to nanoparticles and not that of the released dye. In a previous study, another fluorescence dye, 6-coumarin, which was encapsulated into PLGA nanoparticles as a marker for cellular uptake of nanoparticles, was characterized for the dye release by incubating a suspension of the dye-loaded nanoparticles in the presence of olive oil at 37° C. The dye release from nanoparticles under these conditions was only 0.6% in 48 hours (Desai et al. (1997) Pharm. Res., 14:1568-1573). The release of hydrophobic compounds such as the dyes used herein depends on their loading. Since the dye loading is significantly lower (0.05% for 6-coumarin and 0.1% for NIR dye) than the threshold loading (~10% to 30% w/w, depending upon the polymer composition and characteristics of the drug molecules) required for rapid release (Makadia et al. (2011) Polymers, 3:1377-1397), the incorporated dyes could act as a marker for nanoparticles. The uptake of 6-coumarin dye-loaded nanoparticles was validated by transmission electronic microscopy of cells (Panyam et al. (2003) Int. J. Pharm., 262:1-11). Since, 6-coumarin dye has been extensively used as a marker for PLGA-based nanoparticles to study their cellular uptake and intracellular trafficking (Trapani et al. (2015) Colloids Surf. B Biointerfaces, 127:79-88). Nonetheless, further confirmation of nanoparticle penetration in the skin layers by some other methods, such as electronic microscopy to show the presence of actual nanoparticles, could be performed.

Maestro™ images were taken of specimen pairs mounted between glass slides (FIG. 2A). Fluorescence signal was visualized in two ways: first, translated to heat maps (FIG. 2B), with warm colors representing high fluorescence signal and cool colors representing low fluorescence signal), and second, with near-infrared signal shown as a single color (red) of varying intensity (FIG. 2C). Both demonstrate clear diffusion of near-infrared signal through the treated specimen.

To determine the depth of penetration by dye-containing nanoparticles into the skin, the fluorescence signal of the near-infrared dye was quantified both in total for each specimen and for each of thirty 0.5 mm-wide, vertical regions spanning the cross-section of the specimen (FIG. 3A). The digital sectioning data for each incubation group were compiled, and corresponding control measurements were subtracted from treated specimen measurements, to chart average signal diffusion through these specimens for each incubation time group (FIG. 3B). The fluorescence signal in treated specimens was at a peak on the surface of the skin, where some residue of cream and nanoparticles will remain even after the cream has been manually removed. The signal also shows the penetration of nanoparticles through the skin layers, with an almost exponential decrease in signal intensity with the depth of the skin. The control specimens where only cream was applied displayed insignificant signal throughout the skin layers, indicating that there is no near-infrared background signal from the cream or from the skin itself.

Note that the images in FIG. 2 show that, for a particular specimen, the distribution of nanoparticles is not uniform even in the same layer of the skin. Individual specimens may exhibit more and less intense small regions of near-infrared fluorescence signal at different locations, likely due to either 1) their specific distribution of fibroblast, adipose and other cell types, or 2) localization of nanoparticles into hair follicles. It has been known that nanoparticles can diffuse through hair follicles and from there to the skin (Prow et al. (2011) Adv. Drug Deliv. Rev., 63:470-491; 22. Alvarez-Roman ET AL. (2004) J. Control. Release, 99:53-62). Inside follicles, the stratum corneum is present but is thinner, and thus presents a less well-armored barrier. The most likely other pathway for diffusion of nanoparticles is through the sweat glands, which reach into the dermis and may have an inner diameter of 10-100 μm (Wilke ET AL. (2007) Int. J. Cosmet. Sci., 29:169-179). Application of cream would not have disrupted the epidermis to cause nanoparticles to penetrate the skin layer. Diffusion of PLGA-based nanoparticles (size ~170 nm) loaded with dehydroepiandrosterone (DHEA), an endogenous hormone, through skin layers in pig skin tissue and human skin culture has been shown as well as increased synthesis of collagen in human skin tissue following treatment with DHEA-loaded nanoparticles (Wilke et al. (2007) Int. J. Cosmet. Sci., 29:169-179; Badihi et al. (2014) J. Control. Release, 189:65-71). Protoporphyrin, a photosensitizer, loaded in PLGA-NPs (size 290 nm) has also demonstrated higher delivery of protoporphyrin to mouse skin in vivo than protoporphyrin in solution following topical application (Da Silva et al. (2013) Photochem. Photobiol., 89:1176-1184). Further study could attempt to quantify the clustering of near-infrared signal readings around visible follicles or sweat glands. However, even if nanoparticle penetration does take place through follicles or sweat glands, this would not negate the value of nanoparticles in keeping their contents stable for long enough to reach a deeper target or to deliver a sustained-release dose in the skin layers.

Although the digital sectioning indicates that the nanoparticles have penetrated up to 10-12 mm into the skin, this distance is amplified because of the compression of the sample (after incubation with nanoparticles has been completed) within the glass mounting prior to imaging. However, by measuring specimens with a millimeter rule and comparing the original thickness of each specimen with its thickness after mounting, one can estimate demarcations of different layers of the skin as reflected in Table 1. Note that these are estimates only, based on the average thickness of these layers in normal skin and overall stretching of the skin tissue when placed between the glass slides for imaging (Smij s et al. (2011) Nanotechnol. Sci. Appl., 4:95-112; Zhang et al. (2010) Int. J. Pharm., 402:205-212; Sandby-Moller et al. (2003) Acta Dermato-Venereol., 83:410-413). Further, the assumption was made that the stretching of the different layers of the skin when placed between the glass slides is proportional. Further microscopic analysis would be required to accurately determine the boundaries between skin layers. Nonetheless the analysis provides gross estimation of nanoparticle penetration into different layers of the skin.

TABLE 1

Estimated layer divisions in mounted skin specimens and diffusion of nanoparticles through different layers. The epidermal surface is represented by the first six sections, which is enough to encompass the entire surface no matter how uneven. The 1-2 mm dermis is represented by the following twelve sections, and the inner hypodermis by the remaining twelve sections.

| Region | Original Thickness | Multiple Applied | Thickness After Mounting | Multiple Calculated | Digital Sections | % of Total Signal: 3 h* | % of Total Signal: 24 h* |
|---|---|---|---|---|---|---|---|
| Entire sample | 5-6 mm | — | 15 mm | 3× | — | — | — |
| Epidermis | 100 μm | 3× | 300 μm | — | 1-6 | 59% | 55% |
| Dermis | 1-2 mm | 3× | 3-6 mm | — | 7-18 | 41% | 40% |
| Hypodermis | 3-4 mm | 3× | 9-12 mm | — | 19-30 | 0% | 5% |

*Total signal for each skin layer is the sum of average fluorescence signals (treated less control) for the sections assigned to that layer.

Imaging of signal intensity of skin specimens demonstrated that nanoparticles containing NIR dye, when mixed with cream and applied to human cadaver skin, were able to penetrate into different layers of the skin. The penetration showed an almost exponential decay in signal intensity with the depth of the tissue. Nanoparticles can, therefore, be used for delivery of different therapeutics through the skin layers for treating medical conditions or for cosmetic purposes. Nanoparticles could particularly be effective for delivery of macromolecules such as proteins and peptides, which do not diffuse through the skin easily and are unstable. Further, nanoparticles can sustain the drug effect, which can enhance the therapeutic efficacy of certain drugs that require chronic treatment.

Example 2

Materials and Methods

Nanoparticles were prepared by using a biodegradable polymer, typically using poly (D,L-lacitide co-glycolide) (PLGA), containing an insert plasticizer such as dimethyl tartaric acid (DMT), triethyl citrate, or others suitable plasticizer and using multiple emulsion solvent evaporation methods. Each milligram of the formed nanoparticles contains 150-250 µg (typically about 196 µg (~427 U)) of catalase (CAT) with an estimated release rate of 2-6 U/day (typically about 4 U/day) or 100-200 µg (typically about 128 µg (~583 U)) of superoxide dismutase (SOD) with an estimated release rate of 5-15 U/day (typically about 10 U/day). The SOD and catalase nanoparticles are stable in anhydrous cream are various temperatures for long periods of time (e.g., greater than 39 days), although the catalase nanoparticles lose activity over time at 40° C. and higher.

Experiments in zebrafish embryos show that to completely control $TiO_2$ NPs-induced oxidative stress related death, a 2:1 ratio of Pro-NP™ to $TiO_2$ NPs may be used. The protective effect was seen as low as 0.5:1, but can vary from 0.01 to 10. Based on experiments in rodent tissue, protection is seen by pre-treating skin samples with Pro-NP™ in amounts of 10 to 200 µg Pro-NP™ (2:1 ratio of CAT-NPs and SOD-NPs with a range of 0.5:1 to 3:1) for ~10 minutes to several hours in advance of exposure to UV rays.

Results

It is known that the UV radiation from the sun induces oxidative stress and generates free radicals that are damaging to skin (e.g., the photoaging effect) and also increases the risk of skin cancer. The transport of Pro-NP™ incorporated in a cream following its topical application was demonstrated hereinabove in cadaver skin (see Example 1). The protective effect of Pro-NP™ was also tested in different model systems including in rat and mouse skin, and zebrafish embryos. In the zebrafish model, embryos/fish were exposed to simulated sunlight UV rays in the presence of titanium dioxide ($TiO_2$) nanoparticles. $TiO_2$ nanoparticles, which are used in sunscreen products, have been reported to possess photocatalytic activity that triggers the generation of reactive oxygen species (ROS) in the presence of UV light. Excessive production of ROS causes cellular protein and DNA damage triggers inflammatory response and cell death. The results shown hereinbelow in zebrafish demonstrate that Pro-NP™: a) is nontoxic even at high doses, b) protects zebrafish from $TiO_2$ nanoparticle-induced mortality in a dose-dependent manner, and c) show 100% protection in ~1:2 w/w ratio when combined with $TiO_2$. Rat and mouse skin also showed reduction in the ROS activity following UV exposure in the Pro-NP™ treated groups. The zebrafish embryo model, however, is the most effective in demonstrating the protective effect of Pro-NP™ under relevant conditions. Based on the results presented herein, Pro-NP™ can be used in sunscreen products to protect skin from the $TiO_2$-sun light-induced oxidative stress. In addition, the data demonstrates that Pro-NP™ may be delivered to the skin (e.g., in a topical composition or skin care product) to keep or maintain healthy skin. Indeed, protective antioxidant levels in the skin decrease with ageing. This drop in antioxidant levels is responsible, at least in part, for ROS-mediated changes in extracellular matrix structure (e.g. collagen) that causes skin wrinkling.

The protective effect of Pro-NP™ was tested in a zebrafish model. Zebrafish is an established model for evaluating nanocosmetics and nanomedicines (see, e.g., Beck et al. (2011) Nanocosmetics and Nanomedicines: New Approaches for Skin Care, Springer). A series of preliminary experiments were performed to optimize conditions for testing the protective efficacy of Pro-NP™ in this model. Specifically, these experiments included the dose of $TiO_2$, conditions of embryos (corinated vs. decorinated), exposure time to the light, and treatment time and doses of Pro-NP™ to be tested. Embryos were cultured and exposed to light as described (Bar-Ilan, et al. (2012) Nanotoxicology, 6(6):670-9).

The data shown in FIG. 4A demonstrate that Pro-NP™, even at 600 µg/ml concentration, is nontoxic to embryos and zebrafish. These results are consistent with other data with these nanoparticles in various cell lines including in human neurons (Singhal et al. (2013) Cell Death Dis., 4:e903). The data in FIG. 4B demonstrate that $TiO_2$ nanoparticles in the presence of UV radiation cause ~60% zebrafish mortality whereas when used along with Pro-NP™ in the ratio of 1:2 $TiO_2$: Pro-NP™, only 10% mortality was seen, which is close to the mortality of fish under normal conditions. Thus, Pro-NP™ completely neutralized the deleterious effect of $TiO_2$. FIG. 4C provides representative images of zebrafish grown in the presence of $TiO_2$ and exposed to simulated sun light showing significant abnormality (e.g. growth is inhibited and the fish developed pericardial edema), whereas those cultured in the presence of $TiO_2$:Pro-NP™ look similar to control zebrafish that were cultured under normal conditions in fish water.

The effect of Pro-NP™ in mitigating ROS levels following UV exposure in rat and mouse skin was also determined. Mostly freshly harvested skin sections were used. Briefly, the general protocol was as follows. The epidermal surface of squares receiving treatment was coated with 250 µg of Pro-NP™ in a thick resuspension in 20 µL of ultrapurified water. Squares were placed in individual well markings inside the lid of a 48-well plate, each resting on 50 µL of phosphate-buffered saline (PBS). Plates were incubated at 37° C. for 2-3 hours and then exposed to ultraviolet light for 30 seconds (24 mJ/cm$^2$). Specimens remained positioned in the lid of the 48-well plate for UV exposure in order to avoid interference with UV rays by the sides of the relatively deep wells. UV light components were UVA/UVB/UVC in the proportions 16%/74%/10%. Plates were incubated for 2 hours after UV exposure and then specimens were placed in the wells of a clean 48-well plate and assayed for reactive oxygen species using a one hour incubation with the CellROX® Deep Red Reagent. Assay results were imaged and quantified using the Maestro™ EX In Vivo Fluorescence Imaging System.

As seen in FIGS. 5A and 5B, both rat and mouse skin demonstrated a reduction in reactive oxygen species (ROS) when Pro-NP™ were applied to the skin two to three hours before ultraviolet radiation exposure. Fluorescence signal maps of the skin specimens (approximately 5 mm$^2$) were also obtained. For mouse specimens receiving control (BSA) nanoparticles, the average fluorescence signal counts/pixel was 412. However, the average fluorescence signal counts/pixel was reduced to 351 when the specimen was treated with antioxidant nanoparticles. Similarly, the average fluorescence signal counts/pixel was reduced from 556 for rat control specimens to 426 for rat specimens treated with antioxidant nanoparticles.

Lastly, FIG. 5C shows the fluorescence signal in mouse skin after nanoparticle treatment and 30 second UV exposure. The data shows that treatment with Pro-NP™ is effective in bringing the elevated levels of ROS following UV exposure to that present in skin that is not exposed to UV radiation.

Example 3

Nonmelanoma skin cancer is the most common cancer in the USA, occurring in 1 of 5 Americans during their lifetime (Robinson, J. K. (2005) JAMA 294:1541-1543; Repetto et al. (2008) Nat. Protoc., 3(7):1125-1131). The incidence of skin cancer is rising as well, due to increased exposure to ultraviolet (UV) irradiation, the primary cause of approximately 90% of skin cancers (Karia et al. (2013) J. Am. Acad. Dermatol., 68(6):957-966). Excessive UV radiation exposure to the skin results in oxidative stress that can overwhelm the natural antioxidant defenses of the skin (Bickers et al. (2006) J. Invest. Dermatol., 126(12):2565-2575; Madson et al. (2006) Am. J. Pathol., 169(4):1402-1414). This leads to significant and rapid generation of reactive oxygen species (ROS). ROS can cause DNA damage, lipid peroxidation, and most importantly, activation of oncogenic signaling pathways (Bickers et al. (2006) J. Invest. Dermatol., 126(12):2565-2575; Cadet et al. (2015) Photochem. Photobiol., 91(1):140-155). The ability of human skin to neutralize excess ROS effect is driven by the presence of two key enzymes, superoxide dismutase (SOD) and catalase (CAT), as well as several vitamins and co-factors (Godic et al. (2014) Oxid. Med. Cell Longev., 2014:860479; Pandel et al. (2013) ISRN Dermatol., 2013:930164). However, this antioxidant defense mechanism of skin is overwhelmed by excessive and chronic production of ROS due to prolonged UV exposure (F'Guyer et al. (2003) Photodermatol. Photoimmunol. Photomed., 19(2):56-72). It has also been shown that there is a decrease in cutaneous SOD and CAT levels following UV exposure (Shindo et al. (1993) J. Invest. Dermatol., 100(3):260-265), which is considered an early event in the development of skin cancers (Robbins et al. (2014) Antioxid. Redox Signal 20(10):1628-1645; Robbins et al. (2011) Enzyme Res., 2011:409295).

Because about 90% of nonmelanoma skin cancers, including squamous cell carcinoma, are associated with exposure to UV radiation from the sun (Koh et al. (1996) Arch. Dermatol., 132(4):436-443), skin cancer prevention via mitigating the effects of UV is an effective strategy. Currently used sunscreens and antioxidants are not adequate to prevent or protect against UV radiation. Sunscreens are particularly poor at blocking the long wavelength UVA that produces much of the ROS, while antioxidants typically used to protect skin have poor stability and do not penetrate the skin to reach the cells that are at risk for oncogenic transformation (Green et al. (1999) Lancet 354(9180):723-729; Green et al. (2011) J. Clin. Oncol., 29(3):257-263; Saeidnia et al. (2013) Toxicol. Appl. Pharmacol., 271(1):49-63; Yanagida et al. (2012) Carcinogenesis 33(9):1754-1761; Vilela et al. (2012) Eur. J. Pharm. Biopharm., 80(2):387-392). Recent reports also indicate that $TiO_2$ nanoparticles (NPs) used in most sunscreen products as a UV blocking agent acts as photocatalytic agent to produce more ROS, thus causing greater harm to the skin than benefit (Madson et al. (2009) Am. J. Pathol., 174(6):2357-2366). It has been demonstrated that over-expression of ROS scavenging enzymes such as superoxide dismutase (SOD) and catalase (CAT) reduces skin tumor formation in response to oxidative damage-inducing carcinogens (Zhao et al. (2001) Cancer Res., 61(16):6082-6088). However, improved, effective delivery of these antioxidants to the skin is needed for effective prevention of the oxidative stress-induced oncogenic response and, hence, skin cancer.

The EpiDerm™ tissue system (MatTek; Ashland, Mass.) consists of human-derived epidermal keratinocytes which have been cultured to form a multilayered, highly differentiated model of the human epidermis. This tissue model was used to assay the ability of antioxidant nanoparticles to reduce DNA damage (e.g., thymine dimer formation) and proliferation (as determined by the Ki-67 protein—a cellular marker for proliferation) caused by UV exposure. Briefly, tissue samples were treated with carrier only, control nanoparticles, pure enzyme, or antioxidant nanoparticles for 24 hours. The tissue samples were then UV irradiated (150 $mJ/cm^2$) and then grown for another 24 hours. The tissue samples were then fixed and analyzed. n=3 for all samples.

As seen in FIG. 6A, thymine dimers after UV exposure were decreased in tissue samples treated with antioxidant nanoparticles or pure enzyme, but not with vehicle only or control nanoparticles.

As seen in FIG. 6B, the treatment with antioxidant nanoparticles prevented or inhibited proliferation after UV exposure. Chronic exposure to solar UV is known to modulate the expression of proliferation marker Ki-67; a nuclear non-histone protein expressed by proliferating cells (Aziz et al. (2005) Photochem. Photobiol., 81(1):25-31). Increased expansion of proliferating cells, particularly in basal epidermal cell layers is a significant prognostic factor for diagnosis of stage I and stage II melanoma (Gimotty et al. (2005) J. Clin. Oncol., 23(31):8048-8056; Pearl et al. (2007) J. Exp. Clin. Cancer Res., 26(1):109-115). UV exposure resulted in significant increase of percent Ki-67 expressing cells in total basal keratinocytes as determined by immunohistochemical analysis (FIG. 6B). Pretreatment of the skin with Pro-NP™, at both doses resulted in a marked reduction in UV-mediated increase of percent Ki-67+ve cells, whereas no change was observed with control NPs (FIG. 6B). Thus, the data demonstrated the protective efficacy of Pro-NP™ against UV-induced precancerous hyperproliferative responses in human skin.

Human HaCaT skin keratinocytes are a spontaneously immortalized epithelial cell line that is very similar to normal keratinocytes and, therefore, a substitute for primary keratinocytes to evaluate the damaging effects of UV radiation. Several studies have used HaCaT keratinocytes as a preliminary model to evaluate the protective efficacy of naturally occurring antioxidants against UV-induced oxidative damage (Svobodova et al. (2008) Arch. Dermatol. Res., 300(5):225-233; Svobodova et al. (2007) J. Dermatol. Sci., 46(1):21-30; Svobodova et al. (2009) J. Dermatol. Sci., 56(3):196-204). HaCaT keratinocytes also have unlimited growth potential and are easy to grow in the laboratory. In summary, this model serves a quick and easy performance test for use in scale-up and process/reagent changes in formulation.

Human HaCaT skin keratinocytes were either pretreated with Pro-NP™ or post-treated and the percent cell survival was quantified in sham-irradiated and UV-exposed cultures. Cell viability was determined in HaCaT keratinocytes using neutral red dye, based on the ability of viable cells to incorporate and bind the dye in lysosomes (Repetto et al. (2008) Nat. Protoc., 3(7):1125-1131). HaCat keratinocytes were treated with different doses of Pro-NP (100 or 200 μg) either 2.5 hours before UV exposure or immediately after UV exposure and cultured for 18 hours before determining cell viability. Pro-NP™ demonstrated significant dose-dependent protection against UV (FIG. 6C), with greater efficacy using pre-treatment compared to post-UV.

The protective efficacy of pre-treatment and post-treatment with Pro-NP™ against UV radiation in HaCaT keratinocytes was also tested at several doses of Pro-NP™ (50 to 200 μg) and different amounts of UV radiation (50 to 150 $mJ/cm^2$). UV-induced cellular cytotoxicity in HaCaT keratinocytes was measured at 20 hours after UV exposure. Pretreatment with Pro-NP™ significantly prevented UV-mediated decrease in viability of HaCaT keratinocytes at all doses of UV irradiation tested (FIG. 6D). Pro-NP™ at 200 μg dose was the most effective in reducing UV-induced cell death, while control NPs had no protective effect. Similarly, treatment of HaCaT keratinocytes with Pro-NP™ after UV exposure was also effective in protecting against UV-mediated cellular cytotoxicity (FIG. 6D). However, the protective efficacy was slightly lower compared to pre-treatment with Pro-NP™. Hence, these results demonstrate that either pre- or post-treatment with Pro-NP™ rescues keratinocytes cells from UV-induced damage in a dose-dependent manner. More importantly, at the highest dose tested (200 μg), Pro-NP™ treated HaCaT cells had viabilities comparable or higher than keratinocytes unexposed to UV.

UV irradiation generates ROS in skin that results in oxidative damage to DNA producing 8-hydroxyguanine (8-OHdG), a well-established marker for oxidative stress and oxidative DNA lesions detected in human squamous cell carcinoma (Klaunig et al. (2010) Toxicol. Pathol., 38(1):96-109). To determine the protective efficacy of the antioxidant enzyme loaded Pro-NP™, human skin equivalents were mock treated or treated overnight with Pro-NP™ or control NPs at the epidermal surface, then washed, and later exposed to UV radiation (150 mJ/cm$^2$). A commercially available night repair serum was also used as a positive control. UV exposure resulted in significant increase in oxidative damage to DNA as determined by increased expression of 8-OHdG in human skin equivalents through immunohistochemical staining. Pretreatment of the skin with Pro-NP™, however, prevented the increase in expression of 8-OHdG, whereas control NPs showed no protection (FIG. 6E). Interestingly, the advanced night repair serum used as a positive control showed no protection against UV-induced DNA damage. Furthermore, different ratios of SOD and catalase encapsulated in Pro-NP™ were tested to determine the optimal enzyme ratio for protection against UV-induced oxidative damage. It was found that the ratio of 1:2 (SOD to catalase NPs) was optimal for better protection against UV-induced DNA damage.

Penetration studies with fluorescent nanoparticles provided evidence that Pro-NP™ can effectively penetrate into deeper layers of skin. Using human skin equivalents, it was shown that even after about 48 hours after application (24 hours after treatment removal), Pro-NP™ provides substantially high levels of active SOD and catalase in nucleated epidermal cell layers, whereas control treatments show very light staining for SOD and catalase (FIG. 7). Treatment with pure SOD and catalase mixed in lotion provided some signal in the skin, but is largely restricted to non-nucleated superficial stratum corneum layers (FIG. 7).

Collectively, the data indicates that Pro-NP™ has the ability to deliver antioxidant enzymes deep within skin tissue while reducing UV-mediated damage and skin carcinogenesis.

Example 4

Freshly excised porcine ear skin is close to human skin that is routinely used as a model for testing the protective efficacy of several topically applied antioxidants against UV-induced free radicals. Porcine skin biopsies obtained from local slaughterhouse (pig skin, 6 month old animals, external lobe of the ears) were used for the experiments. The skin was washed, the subdermal fat was removed and cut into 2×2 cm pieces before the application of test samples on the epidermal layer.

The skin has an intrinsic antioxidant protection potential (enzymatic and non-enzymatic), which can be measured by electron spin resonance (ESR) spectroscopy. If an active test sample applied to the stratum corneum penetrates to deep layers of skin, it increases the skin antioxidative protection (SAP). Labeling skin epidermis and dermis (by soaking skin on dermis side) with a semi-stable test radical (TEMPO, 2,2,6,6-tetramethyl piperidine-N-oxyl) that reacts with free radicals produces signal intensities detected by ESR spectroscopy, which can be quantitatively expressed as percent SAP values to determine the antioxidant activity in skin (epidermis and dermis).

Using SAP values from ESR spectroscopy, skin antioxidative retention (SAR) potential of a test cosmetic formulation can be effectively measured using appropriate radical probes. SAR value indicates the antioxidative activity of the skin after free radical damage (UV radiation), which evaluates the protective effectiveness of topically applied antioxidants/free radical scavengers. In addition to the assessment of antioxidative activity in skin, the SAR value also validates the penetration of the topically applied antioxidants. The SAR values are expressed in percent and are calculated using the following formula: SAR [%]= $(SAP_{UV,Product} - SAP_{UV,Placebo})/(SAP_{Placebo} - SAP_{UV,Placebo})$.

The study was conducted blinded and the operator was supplied with formulations that were coded. Pro-NP™, control NPs, or placebo (mixed at 2% w/w in anhydrous lotion) were applied on the skin (2 mg/cm$^2$) and allowed to penetrate for definite times (10 minutes, 30 minutes, 4 hours or 18 hours). The skin was then exposed to UV radiation (0.6 MED; Minimal Erythema Dose) to induce free radicals that lead to a decrease in the SAP values up to 59% of the initial value (without UV treatment) of the untreated skin. Irradiation source: UV solar simulator 300 W Oriel (Newport). The irradiances as integrated value over the spectral ranges were E (UVB=280-320)=23.5 W/m$^2$ and E (UVA=320-400 nm)=180 W/m$^2$. The maintenance of the SAP values after UV exposure due to the test product is expressed by the SAR values.

As seen in Table 2, none of the formulations (Pro-NP™ or control NPs) caused an increase of the SAP values with respect to untreated skin without UV irradiation. There is no direct chemical reaction between the actives and the spin marker (TEMPO). The internal standard (1% Tocopherol) did cause an increase of the SAP values before UV irradiation (29% increase with respect to untreated skin). After the UV irradiation, the SAP of the skin was reduced to 63-59% of the non-irradiated control. The UV-induced free radicals decreased the Antioxidative systems of the skin.

The application of a solution containing 1% Tocopherol (positive reference) showed a lower protection of 24% (factor 1,24) after 10 minutes application and a very weak protection after 30 minutes (due to the fast oxidation of Tocopherol inside the skin). This result lays within the range of confidence for the internal standard of the method (20-27%).

The application of Pro-NP™ showed high protective effect against UV-induced free radicals. The reduction of the SAP values of the UV-irradiated skin could be completely avoided by applying the products. This effect was seen after 10 minutes, 30 minutes and 4 hours of application time, indicating a slow release of the actives. After 18 hours only a small effect could be detected, probably due to the death of the skin cells. As expected, the application of the control NPs showed no significant effect compared to the untreated skin.

TABLE 2

SAR values, means. All values are mean values
of at least 4 skin biopsy samples.

| Product | SAR (%) | | | |
|---|---|---|---|---|
| | 10 mins | 30 mins | 4 hrs | 18 hrs |
| Untreated (Placebo) | 0 | 0 | 0 | 0 |
| 1% Tocopherol (Positive Reference) | 20 | 6 | 0 | 0 |
| Control NPs | 3 | 4 | 2 | 0 |
| Pro-NP ™ | 39 | 118 | 139 | 17 |

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of treating, inhibiting, and/or preventing a skin disease or disorder in a subject in need thereof, said method comprising topically administering at least one nanoparticle to the skin of the subject,
wherein said nanoparticle comprises at least one biodegradable polymer and at least one antioxidant enzyme.

2. The method of claim 1, wherein said antioxidant enzyme is catalase or superoxide dismutase.

3. The method of claim 1, wherein said skin disease or disorder is ultraviolet radiation-induced.

4. The method of claim 1, wherein said skin disease or disorder is photoaging, skin cancer, or sunburn.

5. The method of claim 1, further comprising administering at least one other antioxidant.

6. The method of claim 1, further comprising administering at least one metal oxide nanoparticle.

7. The method of claim 1, wherein said biodegradable polymer is poly (lactide-co-glycolide).

8. The method of claim 1, wherein said nanoparticle further comprises at least one plasticizer.

9. The method of claim 8, wherein said plasticizer is dimethyl tartrate.

10. The method of claim 1, wherein said nanoparticle further comprises at least one emulsifier.

11. The method of claim 10, wherein said emulsifier is polyvinyl alcohol.

12. The method of claim 1, wherein said method comprises administering 1) nanoparticles comprising at least one biodegradable polymer and catalase, and 2) nanoparticles comprising at least one biodegradable polymer and superoxide dismutase.

13. The method of claim 12, wherein the ratio of superoxide nanoparticles to catalase nanoparticles is about 1:5 to about 1:1.

14. The method of claim 1, wherein said nanoparticles are formulated by an emulsion solvent evaporation method.

15. The method of claim 12, wherein said biodegradable polymer is poly (lactide-co-glycolide).

16. The method of claim 15, wherein said nanoparticles further comprise at least one plasticizer.

17. The method of claim 16, wherein said plasticizer is dimethyl tartrate.

18. The method of claim 1, wherein said nanoparticle consists of a biodegradable polymer, an antioxidant enzyme, and, optionally, a plasticizer, an emulsifier, or a plasticizer and an emulsifier.

19. A method of treating, inhibiting, and/or preventing a skin disease or disorder in a subject in need thereof, said method consisting of topically administering nanoparticles to the skin of the subject,
wherein said nanoparticles consist of poly(lactide-co-glycolide), an antioxidant enzyme, and, optionally, a plasticizer, an emulsifier, or a plasticizer and an emulsifier.

20. The method of claim 19, wherein the method consists of administering
1) nanoparticles consisting of poly(lactide-co-glycolide), superoxide dismutase, and, optionally, a plasticizer, an emulsifier, or a plasticizer and an emulsifier, and
2) nanoparticles consisting of poly(lactide-co-glycolide), catalase, and, optionally, a plasticizer, an emulsifier, or a plasticizer and an emulsifier.

21. The method of claim 20, wherein the ratio of superoxide nanoparticles to catalase nanoparticles is about 1:5 to about 1:1.

22. The method of claim 20, wherein the ratio of superoxide nanoparticles to catalase nanoparticles is about 1:2.

23. A topical composition comprising 1) a carrier acceptable for topical delivery, 2) nanoparticles comprising at least one biodegradable polymer and catalase, and 3) nanoparticles comprising at least one biodegradable polymer and superoxide dismutase.

24. The composition of claim 23, wherein said biodegradable polymer is poly (lactide-co-glycolide).

25. The composition of claim 23, wherein the ratio of superoxide nanoparticles to catalase nanoparticles is about 1:2.

26. The composition of claim 25, wherein the ratio of superoxide nanoparticles to catalase nanoparticles is about 1:2.

* * * * *